United States Patent
Domiaty et al.

(10) Patent No.: US 10,383,910 B2
(45) Date of Patent: Aug. 20, 2019

(54) METHODS OF INCREASING FERTILITY OF A MALE SUBJECT WITH COSTUS SPECIOSUS EXTRACT

(71) Applicant: King Abdulaziz University, Jeddah (SA)

(72) Inventors: Dalia Mostafa Mohammed Domiaty, Jeddah (SA); Sherifa Shaker Hamed Hassaballa, Jeddah (SA)

(73) Assignee: King Abdulaziz University, Jeddah (SA)

( * ) Notice: Subject to any disclaimer, the term of this patent is extended or adjusted under 35 U.S.C. 154(b) by 478 days.

(21) Appl. No.: 15/346,029

(22) Filed: Nov. 8, 2016

(65) Prior Publication Data
US 2017/0312330 A1  Nov. 2, 2017

Related U.S. Application Data

(60) Provisional application No. 62/328,320, filed on Apr. 27, 2016.

(51) Int. Cl.
| | |
|---|---|
| *A61K 36/9068* | (2006.01) |
| *A61K 36/88* | (2006.01) |
| *A61K 45/06* | (2006.01) |
| *A61K 31/519* | (2006.01) |
| *A61K 31/352* | (2006.01) |
| *A61K 31/551* | (2006.01) |
| *A61K 31/5513* | (2006.01) |
| *A61K 31/7048* | (2006.01) |

(52) U.S. Cl.
CPC ............ *A61K 36/88* (2013.01); *A61K 31/352* (2013.01); *A61K 31/519* (2013.01); *A61K 31/551* (2013.01); *A61K 31/5513* (2013.01); *A61K 31/7048* (2013.01); *A61K 45/06* (2013.01)

(58) Field of Classification Search
CPC .................................................. A61K 36/9068
USPC ......................................................... 424/756
See application file for complete search history.

(56) References Cited

FOREIGN PATENT DOCUMENTS

| CN | 1559502 A | 1/2005 |
|---|---|---|
| CN | 102836324 A | 12/2012 |
| CN | 103272162 A | 9/2013 |
| CN | 104399053 A | 3/2015 |

OTHER PUBLICATIONS

Deka et al. "Ethnobotanicaly Important Medicinal Plants of Kamrup District, Assam, India, Used in Fertility Treatment", International Research Journal of Pharmacy, 2013, 4 (3). (Year: 2013).*
Soliman et al. "Light and Electron Microscopic Study on the Effect of Antischrenic drugs on the Structure of Seminiferous Tubules of Adult Albino Rats", Folia Histochemica Et Cytobiologica vol. 52, No. 4,2014 pp. 335-349 (Year: 2014).*
Sari et al. "Evaluation of anti-fertility effect of aqueous extract of Costus speciosus (Koen.) J.E. Smith rhizome in mice" Conference on Pharmacy and Advanced Pharmaceutical Sciences. (Year: 2016).*
Deka J., et al., "Ethnobotanical important medicinal plants of Kamrup Istrict, Assam, India, used in fertility treatment" International Research. Journal of Pharmacy, vol. 4(3), 2013, pp. 229-232.
B. Akila, "A Clinical Trial to Study the Safety and Efficacy of Chandrakanthi Choornam in Patients With Low Sperm Count" https://clinicaltrials.gov/ct2/show/record/NCT02234206, Aug. 27, 2014, pp. 1-3.
T. Bu, et al., "Alleviative effect of quercetin on germ cells intoxicated by 3-methyl-4-nitrophenol from diesel exhaust particles" Biomed & Biotechnol, 2012, vol. 13 (4), pp. 318-326.
L. Taepongsorat, et al., "Stimulating effects of quercetin on sperm quality and reproductive organs in adult male rats" Asian J Androl, 2008, vol. 10(2), pp. 249-258.
H.M.Soliman, et al., "Light and electron microscopic study on the effect of antischizophrenic drugs on the structure of seminiferous tubules of adult male albino rats" Folia Histochemica Et Cytobiologica, vol. 52, No. 4, 2014 pp. 335-349.
N. El Sawi, et al., "Assessment of Therapeutic Value of Black Costus (Saussurea lappa) Using Several Parameters" J. Int. Environmental Application & Science, vol. 5(5), 2010, pp. 832-841.

* cited by examiner

*Primary Examiner* — Michael Barker
*Assistant Examiner* — Deborah A Davis
(74) *Attorney, Agent, or Firm* — Oblon, McClelland, Maier & Neustadt, L.L.P.

(57) ABSTRACT

The present disclosure relates to a method of increasing fertility of a male subject, wherein the male subject suffers from reduced fertility resulting from a medication, wherein the medication inhibits sperm cell production by inhibiting spermatogenesis in a testis of the male subject, and wherein the method comprises administering to the male subject an effective amount of an extract of Costus speciosus in combination with the medication to prevent, and/or reduce the inhibition of sperm cell production by the medication to increase the fertility of the male subject.

17 Claims, 23 Drawing Sheets
Specification includes a Sequence Listing.

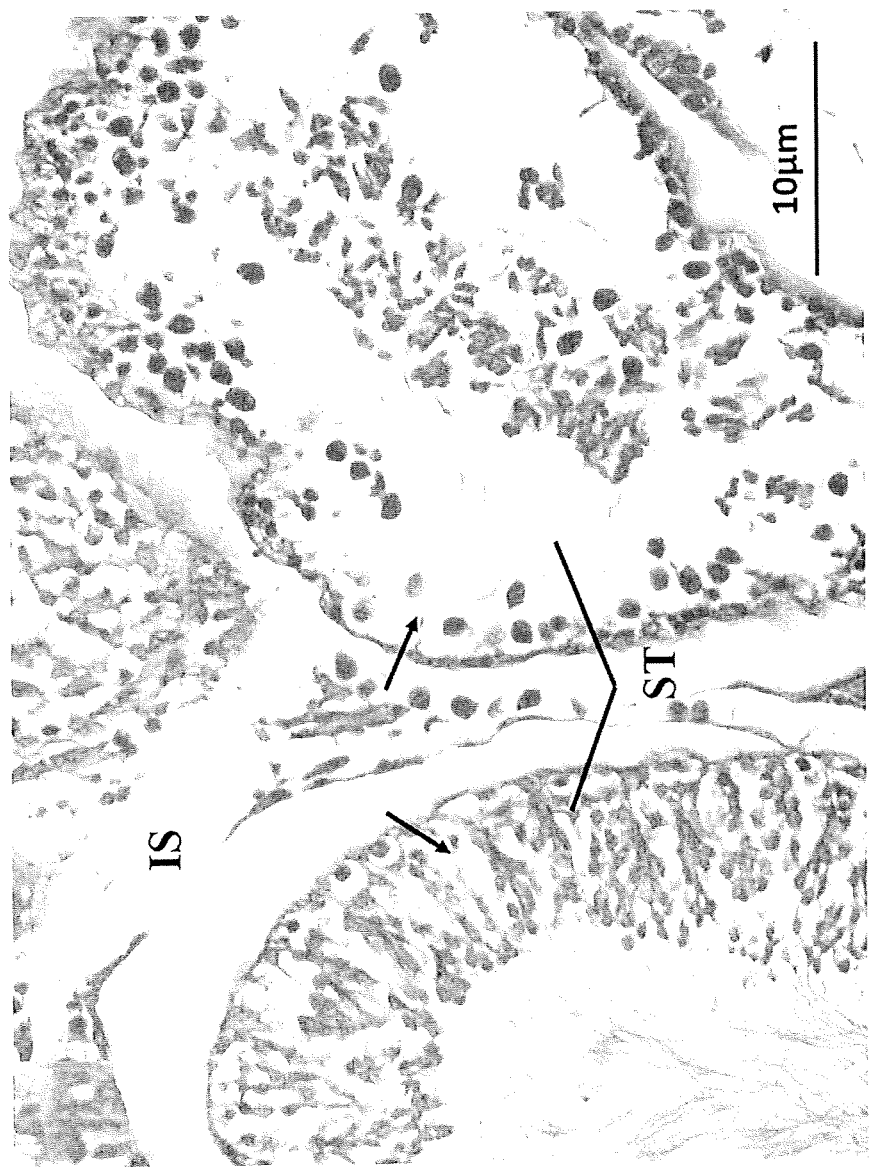

METHODS OF INCREASING FERTILITY OF A MALE SUBJECT WITH COSTUS SPECIOSUS EXTRACT

This application claims the benefit of U.S. Provisional Application No. 62/328,320 filed Apr. 27, 2016, incorporated herein by reference in its entirety.

BACKGROUND OF THE INVENTION

Technical Field

The present disclosure relates to a method of increasing fertility of a male subject (e.g. a male human or a male non-human mammal) who suffers from reduced fertility due to exposure to a medication that inhibits sperm cell production. More specifically, the method includes administering an effective amount of an extract of Costus speciosus in combination with the medication to increase sperm cell production.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, is neither expressly nor impliedly admitted as prior art against the present invention.

Certain medications, for example, antipsychotic drugs for treating schizophrenia such as risperidone, result in sexual dysfunction, reduced sexual activities, or reduced fertility in male animals (e.g. dogs, cats, horses, mice and rats) and male patients.

It is an object of this disclosure to provide a method of increasing fertility of a male subject who suffers from reduced fertility caused by a medication that inhibits sperm cell production in the testis of the male subject. The method includes administering an effective amount of an extract of Costus speciosus in combination with the medication to, for example, increase sperm cell production. The extract of Costus speciosus increases the fertility of the male subject prophylactically and/or therapeutically by preventing, and/or reducing the inhibition of sperm cell production caused by the medication. The male subject may be a male human or a male animal, preferably a male non-human mammal, such as a dog, a cat, a horse, a mouse, or a rat.

BRIEF SUMMARY OF THE INVENTION

The present disclosure relates to a method of increasing fertility of a male subject suffering from reduced fertility resulting from a medication. The method includes administering to the male subject an effective amount of an extract of Costus speciosus in combination with the medication, wherein the medication inhibits sperm cell production by inhibiting spermatogenesis in a testis of the male subject and the administering reduces the inhibition of sperm cell production by the medication.

In one or more embodiments, the male subject is a male human or a non-human male mammal.

In one or more embodiments, the medication inhibiting the spermatogenesis in the testis of the male subject results in at least one selected from the group consisting of (a) deformation and/or atrophy of one or more seminiferous tubules lacking germ cells, (b) exfoliation of spermatogenic cells towards a lumen of a seminiferous tubule, (c) separation of spermatogonia from a basement membrane of a seminiferous tubule, (d) separation of a basal and/or an adluminal cellular compartment in a seminiferous tubule, (e) an increased space between sperm cells and Sertoli cells, (f) necrosis of spermatogenic cells, (g) loss of sperm cells in 70-100% of lumina of seminiferous tubules, (h) aggregation of spermatids in one or more lumina of seminiferous tubules, (i) atrophy of Sertoli cells, and (j) separation of spermatocytes from Sertoli cells.

In one or more embodiments, the medication inhibiting sperm cell production results in a 10-100% reduction in a sperm count of the male subject relative to a baseline sperm count of the male subject before the medication is administered to the male subject.

In one or more embodiments, the medication comprises at least one antipsychotic drug selected from the group consisting of a typical antipsychotic drug and an atypical antipsychotic drug.

In one or more embodiments, the male subject suffers from schizophrenia, and the at least one antipsychotic drug is for treating schizophrenia.

In one or more embodiments, the at least one antipsychotic drug for treating schizophrenia is selected from the group consisting of olanzapine, risperidone, and clozapine.

In one or more embodiments, the extract of Costus speciosus is at least one selected from the group consisting of an extract of Costus speciosus leaves, an extract of Costus speciosus roots, an extract of Costus speciosus flowers, an extract of Costus speciosus rhizomes, and an extract of Costus speciosus stems.

In one or more embodiments, the extract of Costus speciosus is in a form selected from the group consisting of a solid, a semi-solid, and a liquid.

In one or more embodiments, the extract of Costus speciosus comprises at least one selected from the group consisting of tocopherols, phenols, flavanoids, alkaloids, terpenoids, steroids, tannins, phenolic acids, glycosides, carbohydrates, aliphatic hydroxyl ketones, triterpenes, oxoacids, fatty acids, and minerals.

In one or more embodiments, the extract of Costus speciosus comprises at least one flavonoid selected from the group consisting of quercetin, rutin, and apigenin.

In one or more embodiments, the extract of Costus speciosus is administered to the male subject prior to and during a time period of the administration of the medication.

In one or more embodiments, the extract of Costus speciosus is administered to the male subject during a time period of the administration of the medication.

In one or more embodiments, a timeline for the administration of the extract of Costus speciosus overlaps 70-100% of a timeline for the administration of the medication.

In one or more embodiments, the extract of Costus speciosus is administered orally, by inhalation, and/or transdermally.

In one or more embodiments, the extract of Costus speciosus is administered daily, twice a week, weekly, once every two weeks, once every three weeks, monthly, or at a variable interval.

In one or more embodiments, the extract of Costus speciosus is administered as the sole agent to reduce the inhibition of sperm cell production by the medication and/or to increase the fertility of the male subject.

In one or more embodiments, the male subject is a male human and the extract of Costus speciosus is administered in the effective amount of 1-100 mg dry extract/kg body weight/day.

In one or more embodiments, the administration of the extract of Costus speciosus in combination with the medication results in a 10-1000% increase in a sperm count of the male subject as compared to a sperm count of a control male subject administered with the medication but not the extract of Costus speciosus.

In one or more embodiments, the administration of the extract of Costus speciosus in combination with the medication increases a sperm count of the male subject to within a normal range.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 4C is a light micrograph of histological examination of the testis of the rats after 90 days of treatment with the low dose of risperidone (GIII), showing abnormal, disorganized, and atrophied seminiferous tubules (ST), disorganization of germinal epithelium, a loss of spermatogenic cell types (pointed by arrows), and a massive and wide-spread destruction of germ cells as compared to the rat testis of the control treatment group (GI) shown in FIG. 4A. IS: Interstitial space.

DETAILED DESCRIPTION OF THE EMBODIMENTS

Figure 1:
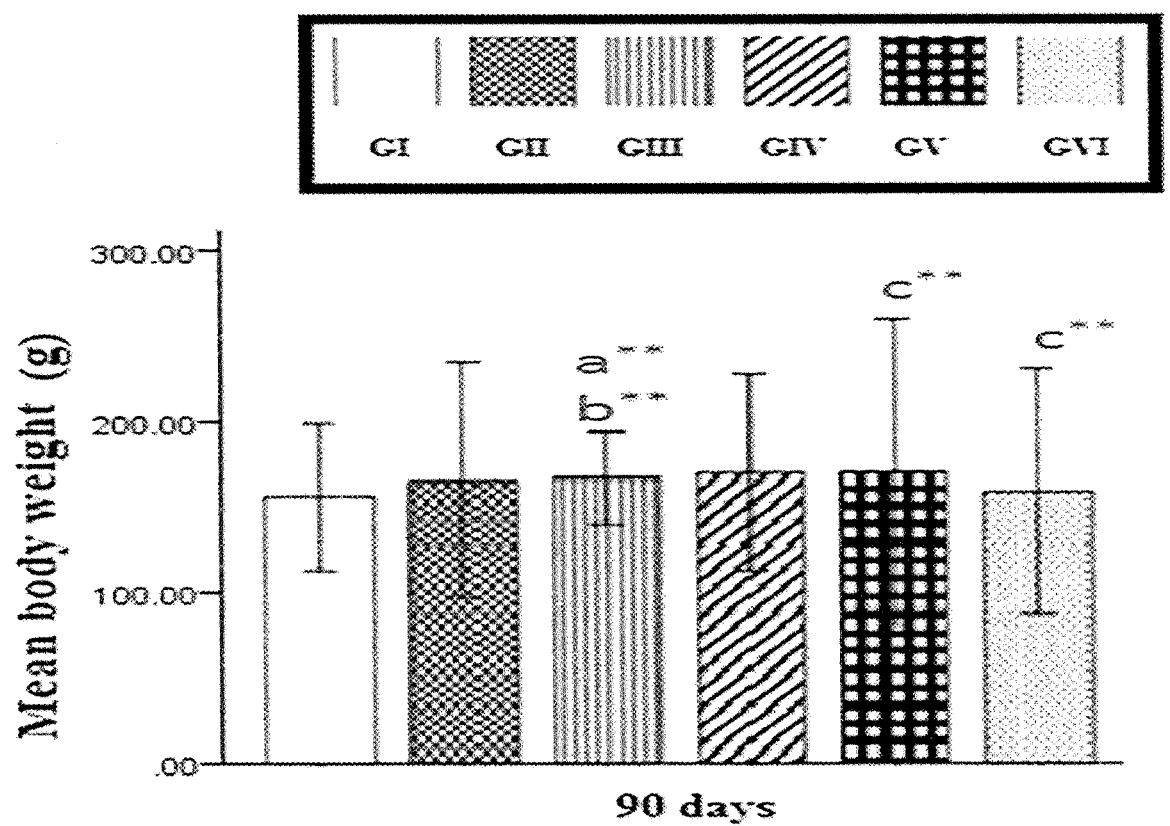
FIG. 1 is a bar graph showing the means±standard deviations of the body weights of the rats of different treatment groups after 90 days of treatment, with GI, GII, GIII, GIV, GV, and GVI representing the first, second, third, fourth, fifth, and sixth treatment group, respectively, and with each treatment group having 5 rats. a, b, and c denote pairwise comparisons between the instant treatment group and GI, GII, or GIII, respectively. ** $P<0.01$.

The present disclosure relates to a method of increasing fertility of a male subject, wherein the male subject suffers from reduced fertility resulting from a medication, wherein the medication inhibits sperm cell production by inhibiting spermatogenesis in a testis of the male subject, and wherein the method comprises administering to the male subject an effective amount of an extract of Costus speciosus in combination with the medication to prevent, and/or reduce the inhibition of sperm cell production by the medication to increase the fertility of the male subject.

In one embodiment, the male subject is a male human. In another embodiment, the male subject is a male animal, preferably a male non-human mammal, such as a dog, a cat, a horse, a mouse, or a rat.

Sperm is the male reproductive cell. A uniflagellar sperm cell that is motile is referred to as a spermatozoon. Sperm cells cannot divide and have a limited life span, but after fusion with egg cells during fertilization, a new organism begins developing, starting as a totipotent zygote. In mammals, sperm develops in the testes and is released from the penis. The spermatozoa of mammals are produced through spermatogenesis inside the male gonads (testes) via mitotic and meiotic divisions. The spermatid stage is where the sperm develops the familiar tail, followed by a further maturation stage to form a fully mature sperm cell, or spermatozoon. Sperm cells are carried out of the male body in a fluid known as semen.

Spermatogenesis is the process in which spermatozoa are produced from male primordial germ cells by way of mitosis and meiosis. In mammals, spermatogenesis occurs in the seminiferous tubules of the male testes in a stepwise fashion. Spermatogenesis is highly dependent upon optimal conditions for the process to occur correctly, and is important for sexual reproduction. The initial cells in spermatogenesis are called spermatogonia, which yield primary spermatocytes by mitosis. The primary spermatocyte divides meiotically (Meiosis I) into two secondary spermatocytes; each secondary spermatocyte divides into two spermatids by Meiosis II. These develop into mature spermatozoa, also known as sperm cells. Thus, the primary spermatocyte gives rise to two cells, the secondary spermatocytes, and the two secondary spermatocytes by their subdivision produce four spermatids which develop into four spermatozoa, the mature male gametes in many sexually reproducing organisms.

Spermatogenesis takes place within several structures of the male reproductive system. The initial stages occur within the testes and progress to the epididymis where the developing gametes mature and are stored until ejaculation. The seminiferous tubules of the testes are the starting point for the process, where stem cells adjacent to the inner tubule wall divide in a centripetal direction—beginning at the walls and proceeding into the innermost part, or lumen—to produce immature sperm. Maturation occurs in the epididymis.

During spermiogenesis, the spermatids begin to form a tail by growing microtubules on one of the centrioles, which turns into basal body. These microtubules form an axoneme. The anterior part of the tail (called midpiece) thickens because mitochondria are arranged around the axoneme to ensure energy supply. Spermatid DNA also undergoes packaging, becoming highly condensed. The DNA is packaged firstly with specific nuclear basic proteins, which are subsequently replaced with protamines during spermatid elongation. The resultant tightly packed chromatin is transcriptionally inactive. The Golgi apparatus surrounds the now condensed nucleus, becoming the acrosome.

Maturation then takes place under the influence of testosterone, which removes the remaining unnecessary cytoplasm and organelles. The excess cytoplasm, known as residual bodies, is phagocytosed by surrounding Sertoli cells in the testes. The resulting spermatozoa are now mature but lack motility, rendering them sterile. The mature spermatozoa are released from the protective Sertoli cells into the lumen of the seminiferous tubule in a process called spermiation.

The non-motile spermatozoa are transported to the epididymis in testicular fluid secreted by the Sertoli cells with the aid of peristaltic contraction. While in the epididymis the spermatozoa gain motility and become capable of fertilization. However, transport of the mature spermatozoa through the remainder of the male reproductive system is achieved via muscle contraction rather than the spermatozoon's recently acquired motility.

In some embodiments, the medication inhibition of the spermatogenesis in the testis of the male subject is indicated by, or results in at least one selected from the group consisting of (a) deformation and/or atrophy of one or more seminiferous tubules lacking germ cells, (b) exfoliation of spermatogenic cells towards a lumen of a seminiferous tubule, (Spermatogenic cells refer to cells that develop in the walls of the seminiferous tubules and include spermatogonia, spermatocytes, and spermatids. The most immature spermatogenic cells are spermatogonia that reside on the basal lamina. The most mature spermatogenic cells are spermatids that are attached to the apical portion of the Sertoli cell and border the lumen of the seminiferous tubule.) (c) separation of spermatogonia from a basement membrane of a seminiferous tubule, (d) separation of a basal and/or an adluminal cellular compartment in a seminiferous tubule, (e) an increased space between sperm cells and Sertoli cells, (f) necrosis of spermatogenic cells, (g) loss of sperm cells in 70-100%, 80-100%, or 90-100% of lumina of seminiferous tubules, (h) aggregation of spermatids, particularly early spermatids, in one or more lumina of seminiferous tubules, (Spermiogenesis refers specifically to the differentiation of early spermatids into mature spermatids just before their release into the seminiferous tubule lumen. Major features of spermiogenesis include elaboration of the acrosome from the Golgi apparatus, condensation and elongation of the nucleus, formation of a motile flagellum, and extensive shedding of the cytoplasm) (i) atrophy of Sertoli cells, (Sertoli cells nurture the developing germ cells by regulating the flow of nutrients and growth factors to the germ cells, and thus the number of Sertoli cells impacts the rate and quality of spermatogenesis) and (j) separation of spermatocytes from Sertoli cells.

In some embodiments, the medication comprises one or more antipsychotic drugs, which may be one or more typical antipsychotic drugs, one or more atypical antipsychotic drugs, or a combination of typical and atypical antipsychotic drugs.

Typical antipsychotic drugs (sometimes referred to as first generation antipsychotics, conventional antipsychotics, classical neuroleptics, traditional antipsychotics, or major tranquilizers) are a class of antipsychotic drugs first developed in the 1950s and used to treat psychosis (in particular, schizophrenia). Typical antipsychotic drugs may also be used for the treatment of acute mania, agitation, and other conditions. Non-limiting examples of typical antipsychotic drugs include fluphenazine, haloperidol, chlorpromazine, promazine, loxapine, and thiothixene.

Atypical antipsychotic drugs (also known as second generation antipsychotics (SGAs)) are a group of antipsychotic drugs used to treat psychiatric conditions. Some atypical antipsychotic drugs have received regulatory approval (e.g. by the FDA of the US, the TGA of Australia, the MHRA of the UK) for schizophrenia, bipolar disorder, autism, and as an adjunct for treating major depressive disorders. Non-limiting examples of atypical antipsychotic drugs include olanzapine, risperidone, quetiapine, ziprasidone, clozapine, asenapine, and paliperidone.

Both typical and atypical antipsychotic drugs tend to block receptors in the brain's dopamine pathways. Atypical antipsychotic drugs are thought to be safer than typical antipsychotic drugs and less likely than the most widely used typical antipsychotic drug haloperidol to cause extrapyramidal motor control disabilities in patients, such as unsteady Parkinson's disease-type movements, body rigidity, and involuntary tremors.

In one embodiment, the male subject suffers from schizophrenia, and the medication comprises one or more antipsychotic drugs, which may be typical antipsychotic drugs, atypical antipsychotic drugs, or a combination of typical and atypical antipsychotic drugs, for treating schizophrenia. Non-limiting examples of the medication for treating schizophrenia include olanzapine, risperidone, and clozapine.

In other embodiments, the medication which is administered to the male subject and inhibits sperm cell production may comprise at least one selected from the group consisting of testosterone (e.g. for the male subject undergoing testosterone replacement therapy), an anabolic-androgenic steroid, a chemotherapy drug, particularly an alkylating agent (e.g. chlorambucil, cyclophosphamide, nitrogen mustard, methotrexate, procarbazine, melphalan, cisplatin, doxorubicin, thiotepa, cytarabine, vinblastine, and vincristine), an antifungal medication (e.g. ketoconazole) and/or an antibiotic medication (e.g. nitrofuran and minocycline), and an ulcer medication (e.g. cimetidine).

*Cheilocostus speciosus*, also known as Costus speciosus or crêpe ginger, is possibly the best known cultivated species of the genus Costus. This plant is native to southeast Asia and surrounding regions, from India to China to Queensland. It is especially common on the Greater Sunda Islands in Indonesia.

Costus speciosus differs from the common ginger by having only one row of spirally arranged leaves. It is a succulent, erect and perennial plant with spreading stems, thick creeping rhizomes, long lanceolate dark green leaves, white fragrant flowers, red fruits, and black seeds. The species reproduces vegetatively by rhizome, by division of culms and stem cuttings, or by seeds dispersed by birds.

In some embodiments, the extract of Costus speciosus is prepared by extracting leaves, roots, flowers, rhizomes, stems, or combinations of the above Costus speciosus parts with a solvent or a series of solvents, such as water and/or organic solvents, non-limiting examples of which include petroleum ether, hexane, cyclohexane, benzene, ethyl acetate, chloroform, acetone, alcohols (e.g. methanol and ethanol), a mixture of organic solvents and water (e.g. a mixture of water and an alcohol), and combinations of organic solvents. The Costus speciosus parts are preferably shade dried and pulverized before the extraction. In a preferred embodiment, the extraction is performed by using a maceration apparatus, a Soxhlet extractor, or a Kumagawa extractor. In some embodiments, the extraction is performed at a temperature of 15-100° C., 25-90° C., 35-80° C., 45-70° C., or 55-60° C. In a preferred embodiment, during the extraction, the exposure of the extract to light is limited or minimized to preserve the activity of phytochemicals responsible for preventing, and/or reducing the inhibition of sperm cell production by the medication.

In one embodiment, the Costus speciosus parts are extracted with a solvent only once. In another embodiment, the Costus speciosus parts are extracted with the same solvent or different solvents successively. For example, the Costus speciosus parts may be successively extracted with a series of solvents, e.g. petroleum ether, cyclohexane, benzene, ethyl acetate, chloroform, acetone, methanol, and water in a pre-determined solvent sequence, for example, starting with the least polar solvent followed by the solvents of increasing polarities. When successive extractions are performed, the extracts from successive extractions may be combined and dried, and optionally the resulting combined dried extract may be resuspended in a suitable solvent, such as water, a beverage, a sodium carboxymethyl cellulose solution, an alcohol (e.g. methanol and/or ethanol), or a mixture of water and an alcohol. Thus, the extract of Costus speciosus may be in a form of a solid (e.g. a tablet, a lozenge, a capsule, or a powder), a semi-solid (e.g. a gel, a paste, a lotion, or a cream), or a liquid (e.g. a solution, a spray, or a beverage). In some embodiments, the extract of Costus speciosus comprises at least one selected from the group consisting of ascorbic acid, beta-carotene, glutathione, tocopherols (e.g. alpha-tocopherol), phenols, flavonoids (e.g. quercetin, quercitrin, rutin, and/or apigenin), alkaloids, terpenoids, steroids, tannins, phenolic acids (e.g. 2.4-dihydroxybenzoic acid), glycosides (e.g. saponins), carbohydrates, aliphatic hydroxyl ketones, triterpenes, oxoacids, fatty acids, abscisic acid, corticosteroids, and minerals (e.g. copper and zinc). In a preferred embodiment, the extract of Costus speciosus comprises flavonoids, phenolic acids, and/or minerals.

The content of flavonoids may vary in the extract of Costus speciosus, depending on the growing sites of Costus speciosus, the parts of Costus speciosus used to make the extract, the freshness of the Costus speciosus parts, and the season of harvest of Costus speciosus parts. In some embodiments, rutin is present in the extract of Costus speciosus at a concentration of 800-4500, 1000-4000, 1500-3500, 2000-3000 µg/g dry extract. In other embodiments, quercitrin is present in the extract of Costus speciosus at a concentration of 800-10,000, 1000-9000, 1500-8500, 2000-8000, 2500-7500, 3000-7000, 3500-6500, 4000-6000, or 4500-5500 µg/g dry extract. In still other embodiments, quercetin is present in the extract of Costus speciosus at a concentration of 100-400, 150-350, or 200-300 µg/g dry extract.

The extract of Costus speciosus may be administered to the male subject orally, by inhalation, and/or transdermally (topically).

In some embodiments, a pharmaceutical formulation comprising the extract of Costus speciosus and at least one pharmaceutically acceptable carrier and/or excipient is administered to the male subject. The phrase "pharmaceutically acceptable carrier or excipient" as used herein means a pharmaceutically acceptable material, composition or vehicle, such as a liquid or solid filler, diluent, binder, manufacturing aid (e.g., lubricant, talc magnesium, calcium or zinc stearate, or steric acid), or solvent encapsulating material, involved in carrying or transporting the extract from one organ, or portion of the body, to another organ, or portion of the body. Each carrier must be "acceptable" in the sense of being compatible with the other ingredients of the formulation and not injurious to the male subject. Non-limiting examples of pharmaceutically acceptable carriers and/or excipients include (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The extract of Costus speciosus is contemplated to possess the prophylactic effect of preventing the medication from inhibiting sperm cell production when the extract of Costus speciosus is administered before the start of the administration of the medication, and/or the therapeutic effect of reducing the inhibition of sperm cell production by the medication when the extract of Costus speciosus is administered at the same time of or after the administration of the medication. The above effects of the extract of Costus speciosus disclosed in the present application are unexpected, since "Costus speciosus is empirically used as a traditional male contraception in some areas," and "oral administration of CSRE (Costus speciosus rhizome extract) for 14 days resulted in a significant reduction in spermatozoa level and quality" in male mice that "influence male fertility," as described in Evaluation of Anti-Fertility Effect of Aqueous Extract of Costus speciosus (Koen.) J. E. Smith Rhizome in Mice, Sari I P, Nurrochmad A, and Rahayu S, International Journal of Pharmaceutical and Clinical Research 2016; 8(5), Suppl: 440-444, incorporated herein by reference in its entirety.

In one embodiment, the extract of Costus speciosus is administered to the male subject prior to and during a time period of the administration of the medication. In another embodiment, the Costus extract is administered to the male subject during a time period of the administration of the medication. When the extract of Costus speciosus is administered to the male subject during a time period of the administration of the medication, the Costus extract may be administered concurrently with the administration of the medication (e.g. at the same time or on the same day the medication is administered), or may be administered generally during the same time period in which the medication is administered, although not necessarily concurrently. For example, the extract of Costus speciosus may be administered a number of days (e.g. 1-10 days, 3-8 days, or 4-6 days) after the start of the administration of the medication; the extract of Costus speciosus may be administered on a day or days between the start and the end of the administration of the medication on which the administration of the medication is temporarily suspended, and/or the extract of Costus speciosus may not be administered on a day or days after the start of the administration of the extract of Costus speciosus while the medication is administered on the day or days. In a preferred embodiment, a timeline for the administration of the extract of Costus speciosus overlaps 70-100%, preferably 80-100%, more preferably 90-100% of a timeline for the administration of the medication.

In some embodiments, the extract of Costus speciosus is administered daily, twice a week, weekly, once every two weeks, once every three weeks, monthly, or at a variable interval.

In one embodiment, the extract of Costus speciosus is administered as the sole agent to prevent, and/or reduce the inhibition of sperm cell production by the medication, and/or to increase the fertility of the male subject without administering to the male subject any other male fertility enhancing agents, e.g. non-Costus root components of the Chinese medicine composition, such as motherwort, epimedium herb, perilla leaf, or other substances disclosed in Chinese Patent Application Publication No. CN 103272162 A, incorporated herein by reference in its entirety; non-Costus root components of the Chinese medicine composition, such as nidus vespae, polygonum multiflorum, cinnamon, or other substances disclosed in Chinese Patent Application Publication No. CN 1559502 A, incorporated herein by reference in its entirety; and/or 24 non-Costus speciosus root components of Chandrakanthi Choornam, such as Curculigo orchioides-rhizome, Maerua arenaria-tuber, Glycyrrhiza glabra-root, or other substances disclosed in A Clinical Trial to Study the Safety and Efficacy of Chandrakanthi Choornam in Patients With Low Sperm Count, Dr. B. Akila, Aug. 27, 2014, ClinicalTrials.gov Identifier: NCT02234206, incorporated herein by reference in its entirety.

In another embodiment, the extract of Costus speciosus and other male fertility enhancing agents, such as those exemplified above, are administered together to the male subject. In some embodiments, the ratio of the dry weight of the extract of Costus speciosus to the weight of the other male fertility enhancing agents is in the range of (99-50): (1-50), (90-60): (10-40), or (80-70): (20-30). The effective amount of the extract of Costus speciosus administered in combination with the medication to prevent, and/or reduce the inhibition of sperm cell production by the medication may vary without limitation, depending on, for example, the origin of the Costus speciosus plant, the parts of the Costus speciosus plant and the solvents used for making the extract, the extract preparation method and condition (e.g. extraction temperature and duration, light exposure of the extract, etc) that may affect the activity of phytochemicals responsible for preventing, and/or reducing the inhibition of sperm cell production by the medication, the dose of the medication administered to the male subject, the species, age, weight, size, and medical conditions (e.g. the tolerance of the extract of Costus speciosus) of the male subject, the route of the administration, the absorption, distribution, metabolism, and excretion of phytochemicals responsible for preventing, and/or reducing the inhibition of sperm cell production by the medication in the body of the male subject. A skilled artisan is able to determine the effective dose and frequency of the administration of the extract of Costus speciosus based on the above mentioned factors and other considerations. When the male subject is a male human, preferably a male adult human, the effective amount of the extract of Costus speciosus may be 1-100, 5-90, 10-80, 20-70, 30-60, or 40-50 mg dry extract/kg body weight/day.

Since the inhibition of sperm cell production by the medication and the de-inhibition by the extract of Costus speciosus affect the concentration of sperms in semen, i.e. the sperm count, in the male subject, in some embodiments, the inhibition of sperm cell production by the medication results in a 10-100%, 20-90%, 30-80%, 40-70%, or 50-60% reduction in a sperm count of the male subject relative to a baseline sperm count of the male subject before the medication is administered to the male subject. In other embodiments, the administration of the extract of Costus speciosus in combination with the medication results in a 10-1000%, 50-800%, 100-600%, 200-500%, or 300-400% increase in a sperm count of the male subject as compared to a sperm count of a control male subject administered with the medication but not the extract of Costus speciosus. The control male subject is preferably matched with the male subject in various aspects that may influence the sperm count, such as age, ethnicity, medical and health conditions, body weight and height, testosterone level, life-style habits (e.g. smoking/non-smoking and alcohol consumption), diet choices, and physical activity.

In other embodiments, the administration of the extract of Costus speciosus in combination with the medication increases a sperm count of the male subject to within a normal range. In male humans, a normal sperm count is above 10-35, 15-30, or 20-25 million sperms per milliliter of semen.

Having generally described this invention, a further understanding can be obtained by reference to certain specific examples which are provided herein for purposes of illustration only and are not intended to be limiting unless otherwise specified.

Example 1

Materials and Methods

1. Risperidone:

Risperidone (molecular formula $C_{23}H_{27}FN_4O_2$, Molecular weight 410.4845), also known by its brand name as Risperidal, was obtained from Janssen in the form of an oral solution at a concentration of 1 mg/mL. Experimental animals were treated with risperidone once daily by oral injection with a stomach tube.

2. Preparation of Costus Speciosus Extract:

Costus speciosus roots obtained from herbs shops in Jeddah, Saudi Arabia, were washed, crushed, and pulverized. The root extract of Costus speciosus was prepared by adding 100 ml of boiling water to 10 grams of the pulverized roots in a cup that was subsequently covered and left in the dark for 24 hours. The resulting aqueous root extract of Costus speciosus was filtered (See Domiaty, D. M. (2009): Histological and ultrastructural studies on the effect of Costus plant and Amphotericine B on the lung rats infected by *Aspergillus niger* to manifest the scientific miracles in Sunnah. Master thesis, University of King Abdul alaziz, Jeddah, incorporated herein by reference in its entirety), and the supernatant was collected in a dark bottle and stored at 4° C. Experimental animals were treated with the root extract of Costus speciosus once daily by oral injection with a stomach tube.

3. Experimental Animals:

The experiments in the Examples were conducted on 30 male albino rats of the Wister strain with an age range of 40-45 days (approximately 6 weeks) and a weight range of 68-122 g. The rats were obtained from the Animal House, Faculty of Pharmacy, King Saud University. The rats were provided feed and water, and bred in a private room with a temperature of 24±2° C., a relative humidity of 55±5%, and a 12-hour light/12-hour dark cycle.

4. Treatment of Experimental Animals:

The experimental animals were divided into six treatment groups as follows:

The first treatment group (GI) was a control treatment group composed of 5 rats that were given distilled water orally throughout the experiment.

The second treatment group (GII) was composed of 5 rats that were orally administered with only the root extract of Costus speciosus at a dose of 2 mg/kg body weight/day.

The third treatment group (GIII) was composed of 5 rats that were orally administered with risperidone at a low dose of 1 mg/kg body weight/day.

The fourth treatment group (GIV) was composed of 5 rats that were orally administered with both risperidone at the low dose of 1 mg/kg body weight/day and the root extract of Costus speciosus at 2 mg/kg body weight/day.

The fifth treatment group (GV) was composed of 5 rats that were orally administered with risperidone at a high dose of 2 mg/kg body weight/day.

The sixth treatment group (GVI) was composed of 5 rats that were orally administered with both the high dose of risperidone at 2 mg/kg body weight/day and the root extract of Costus speciosus at 2 mg/kg body weight/day.

The rats were treated for ninety days, which was the duration of the experiment, and were dissected after 90 days. The blood samples of the rats were collected in special EDTA anticoagulant tubes. Blood tests were done to determine the plasma levels of testosterone. The testes of the rats were excised, placed in a suitable fixative, and prepared for histological, ultrastructural and molecular studies. The doses of risperidone and the root extract of Costus speciosus for the treatments were determined based on several initial experiments.

5. Histological Study:

The rat testes were fixed in 10% neutral buffered formalin (pH 7.2-7.4) for 48 hours (See Hopwood, N.J. (2002): Treatment of the infant with congenital hypothyroidism. *J Pediatr.* 141(6):752-4, incorporated herein by reference in its entirety), followed by dewatering with 70%, 90%, and 100% alcohol and embedding in paraffin wax. The paraffin embedded tissue samples were cut into 3-5 µm-thick paraffin sections with a Rotary microtome. The paraffin sections were laid onto glass slides and stained with hematoxylin-eosin to determine histological changes in the testes under a light microscope (See Bancroft, J. D. & Gamble, M. (2007): Theory and Practice of Histological Techniques. 6th Ed, *Churchill Livingstone., P:* 744, incorporated herein by reference in its entirety).

6. Ultrastructure Study:

Small rat testes specimens (about 1 mm³) were fixed in 4% glutaraldehyde in 0.2 M cacodylate buffer at 4° C. for 24 hours, and then post-fixed with osmium tetraoxide in 0.2 M cacodylate buffer at room temperature. Then the samples were dehydrated in a series of ethanol solutions and in propylene oxide, and embedded in resin. The embedded blocks were cut into 1 µm semi-thin sections with a diamond knife, and the semi-thin sections were stained with toluidine blue. Ultrathin sections were cut by an ultramicrotome, and then the ultrathin sections were stained with lead citrate and uranyl acetate for examination by transmission electron microscopy (See Woods, A. E. & Stirling, J. W. (2002): Electron microscopy: The preparative techniques. In: Theory and practice of histological techniques. 5th Ed. Bancroft, J. D. and Gamble, M Harcourt publishers, Ch. 31, incorporated herein by reference in its entirety).

7. Molecular Study:

7.1. RNA Extraction:

Frozen testicular tissues were thawed on ice, and total RNA was isolated using Qiagen's RNeasy mini kit, cat #74104 (Qiagen Inc., Valencia, Calif., USA) according to the manufacturer's instructions.

7.2. Determination of the Quality and Quantity of the Isolated Total RNA:

The quality of the isolated total RNA was assessed by electrophoresis on a 1% agarose gel based on the integrity of the 28S and 18S rRNA bands after ethidium bromide staining of the agarose gel. Using UV Spectroscopy with a Nano Drop spectrophotometer, the concentration of the isolated total RNA sample was determined by the absorbance at 260 nm ($A_{260\,nm}$), and the purity of the isolated total RNA sample was determined by the ratio of the absorbance at 260 nm to the absorbance at 280 nm ($A_{260\,nm}/A_{230\,nm}$).

7.3. Design of Semi-Quantitative and Quantitative Real-Time (RT) Polymerase Chain Reaction (PCR) Primers:

The sequences of the primers are listed in Table 1.

TABLE 1

Sequences of primers used for the semi-quantitative and quantitative real-time PCR analysis.

| Isoforms | Primers sequence (5'-3') |
|---|---|
| CYP1A1 F | GGG AGG TTA CTG GTT CTG G (SEQ ID NO: 1) |
| CYP1A1 R | ATG AGG CTG TCT GTG ATG TC (SEQ ID NO: 2) |
| CYP2C6 F | GAC CTC ATT CCT ACC AAC CT (SEQ ID NO: 3) |
| CYP2C6 R | CCT CTC CTG CAC ACA TCC (SEQ ID NO: 4) |
| CYP2E1 F | CCT TTC CCT CTT CCC ATC C (SEQ ID NO: 5) |
| CYP2E1 R | AAC CTC CGC ACA TCC TTC C (SEQ ID NO: 6) |
| CYP3A9 F | GGTGTTGTATCACATGGACCAGA (SEQ ID NO: 7) |
| CYP3A9 R | CCAGGAGTGAACAAAATTACTGCA (SEQ ID NO: 8) |
| GAPDH F | GAT GGT GAA GGT CGG TGT G (SEQ ID NO: 9) |
| GAPDH R | ATG AAG GGG TCG TTG ATG G (SEQ ID NO: 10) |

F - Forward,
R - Reverse,
GAPDH - glyceraldehydes phosphate 3-dehydrogenase

The forward and reverse primer sequences for CYP3A9 were obtained from Anakk, S.; Ku, C. Y.; Vore, M. & Strobel, H. W. (2003): Insights into Gender Bias: Rat Cytochrome P450 3A9, 305: 703-709, incorporated herein by reference in its entirety. The forward and reverse primer sequences for GAPDH, CYP1A1, CYP2C6 and CYP2E1 were obtained from Mrozikiewicz, P. M.; Bogacz, A.; Karasiewicz, M.; Mikolajczak, P. L.; Ozarowski, M. A.; Seremak-Mrozikiewicz, A.; Czerny, B.; Bobkiewicz-Kozlowska, T. & Grzeskowiak, E. (2010): The effect of standardized *Echinacea purpurea* extract on rat cytochrome P450 expression level, *Phytomedicine*, 17: 830-833, incorporated herein by reference in its entirety. All of the primers were synthesized by Invitrogen of Life Technologies.

7.4. Quantitative Real-Time PCR:

The isolated total RNA was reverse transcribed to cDNA, which was subjected to quantitative real-time PCR using a quantitative real-time polymerase chain reaction for gene expression detection kit from Qiagen (QuantiTect SYBR Green RT-PCR Kit, cat #204243) according to manufacturer's instructions.

7.5. Semi-Quantitative PCR:

The cDNA prepared in Section 7.4. was subjected to semi-quantitative PCR using the primers listed in Table 1. An aliquot of the PCR product sample as well as a DNA molecular weight marker sample was then subjected to electrophoresis on an agarose gel. After the electrophoresis, the agarose gel was stained with ethidium bromide for visualization and quantification of the PCR product of a specific size resulting from amplification of the cDNA of each of the CYP genes and GAPDH with reference to the DNA molecular weight marker.

8. Statistical Analysis:

Statistical analyses were performed using SPSS software version 21.00. One-way analysis of variance (ANOVA), post-hoc and least significant difference (LSD) were performed for intergroup comparisons. $P>0.05$, $P\leq0.05$, and $P\leq0.001$ were considered non-significant, significant, and highly significant, respectively.

Example 2

Figure 2:
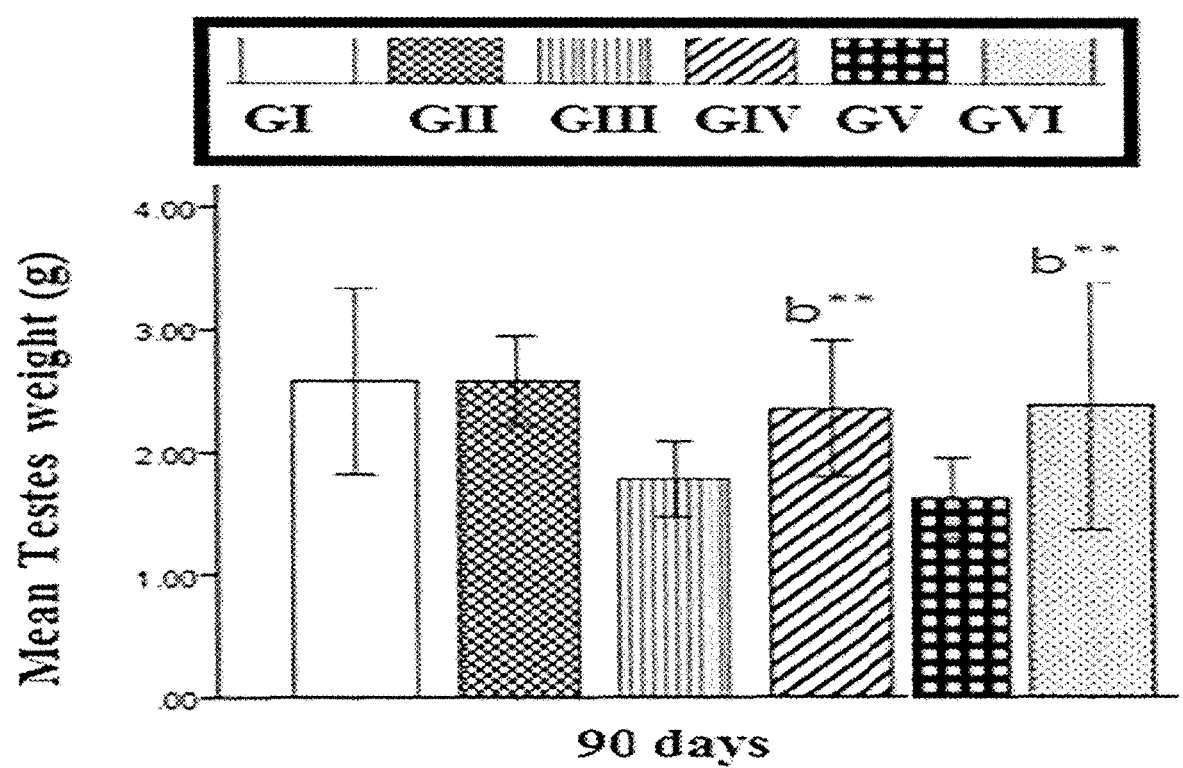
FIG. 2 is a bar graph showing the means±standard deviations of the testes weights of the rats of different treatment groups after 90 days of treatment, with GI, GII, GIII, GIV, GV, and GVI representing the first, second, third, fourth, fifth, and sixth treatment group, respectively, and with each treatment group having 5 rats. b denotes a pairwise comparison between the instant treatment group and GII. ** $P<0.01$.

1. Morphological and Body and Testes Weights Changes:

No mortality or morphological changes were noticed during the experiments in general. Referring to FIG. 1 and FIG. 2, body and testes weights of the treatment groups treated with the root extract of Costus speciosus alone (GII) and with a combination of the root extract of Costus speciosus and risperidone (GIV and GVI) were more or less similar to those of the control treatment group (GI). Referring to FIG. 1, the rats treated with a low dose of risperidone (GIII) displayed a significant increase in body weight compared to the rats of the control treatment group (GI) or of GII treated with only the root extract of Costus speciosus. Additionally, the rats treated with the high dose of risperidone (GV) displayed a significant increase in body weight compared to the rats of GIII treated with the low dose of risperidone. The above significant increases in body weight may be due to risperidone stimulation of appetite via risperidone-induced hormonal changes. By contrast, the rats treated with the high dose of risperidone as well as the root extract of Costus speciosus (GVI) displayed a significant decrease in body weight compared to the rats of GIII treated with the low dose of risperidone.

Referring to FIG. 2, the rats treated with either dose of risperidone (GIII and GV) displayed an insignificant reduction in testes weight relative to the control treatment group (GI). By contrast, the rats treated with both risperidone at the low dose and the root extract of Costus speciosus (GIV) or treated with both risperidone at the high dose and the root extract of Costus speciosus (GVI) displayed a significant decrease in testes weight as compared to the rats of GII treated with only the root extract of Costus speciosus.

Figure 3:
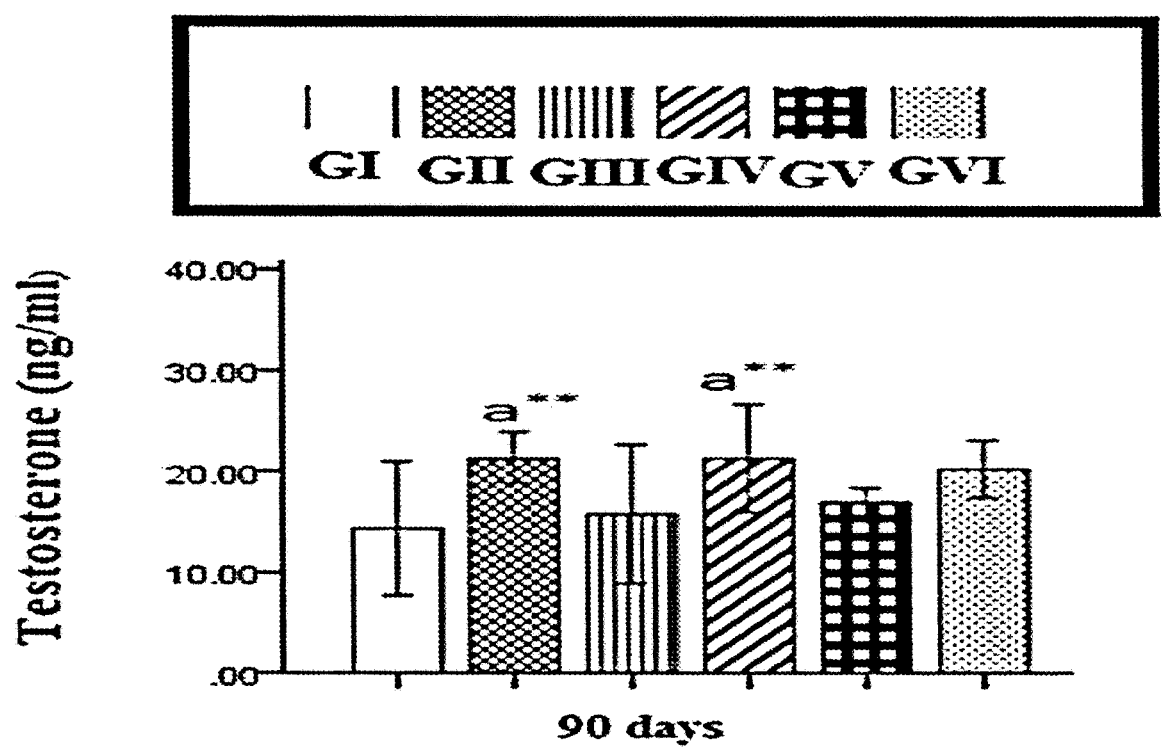
FIG. 3 is a bar graph showing the means±standard deviations of the plasma levels of testosterone of the rats of different treatment groups after 90 days of treatment, with GI, GII, GIII, GIV, GV, and GVI representing the first, second, third, fourth, fifth, and sixth treatment group, respectively, and with each treatment group having 5 rats. a denotes a pairwise comparison between the instant treatment group and GI. ** $P<0.01$.

2. Changes of Bioassay Parameters:

Referring to FIG. 3, treatment of the rats with risperidone only at the low or high dose (GIII and GV) led to an insignificant reduction in the plasma level of testosterone after 90 days as compared to the plasma levels of testosterone in the rats of GIV treated with both risperidone at the low dose and the root extract of Costus speciosus and in the rats of GVI treated with both risperidone at the high dose and the root extract of Costus speciosus, respectively. Additionally, the mean plasma level of testosterone was significantly higher in the rats of (GII) treated with the root extract of Costus speciosus only or in the rats of GIV treated with both the root extract of Costus speciosus and the low dose of risperidone for 90 days relative to that in the rats of the control treatment group (GI), indicating the effect of the root extract of Costus speciosus on improving the fertility of the rats of GII and GIV.

Figure 4A:
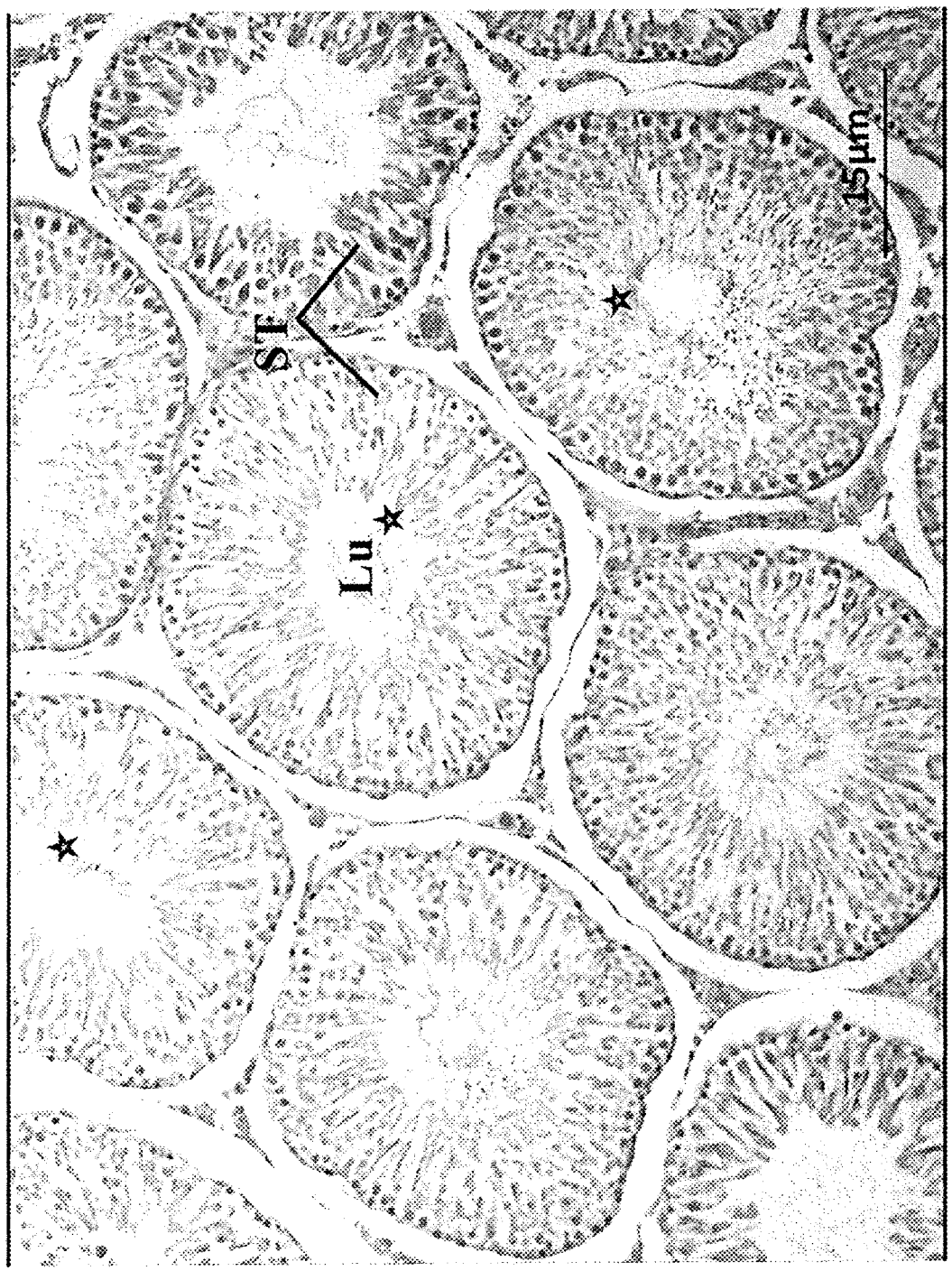
FIG. 4A is a light micrograph of histological examination of the testis of the rats of the control treatment group (GI) after 90 days of treatment, showing normal histological structure of the seminiferous tubules (ST) populated by spermatocytes and late spermatids (*) surrounding the tubular lumen (Lu).
Figure 4B:
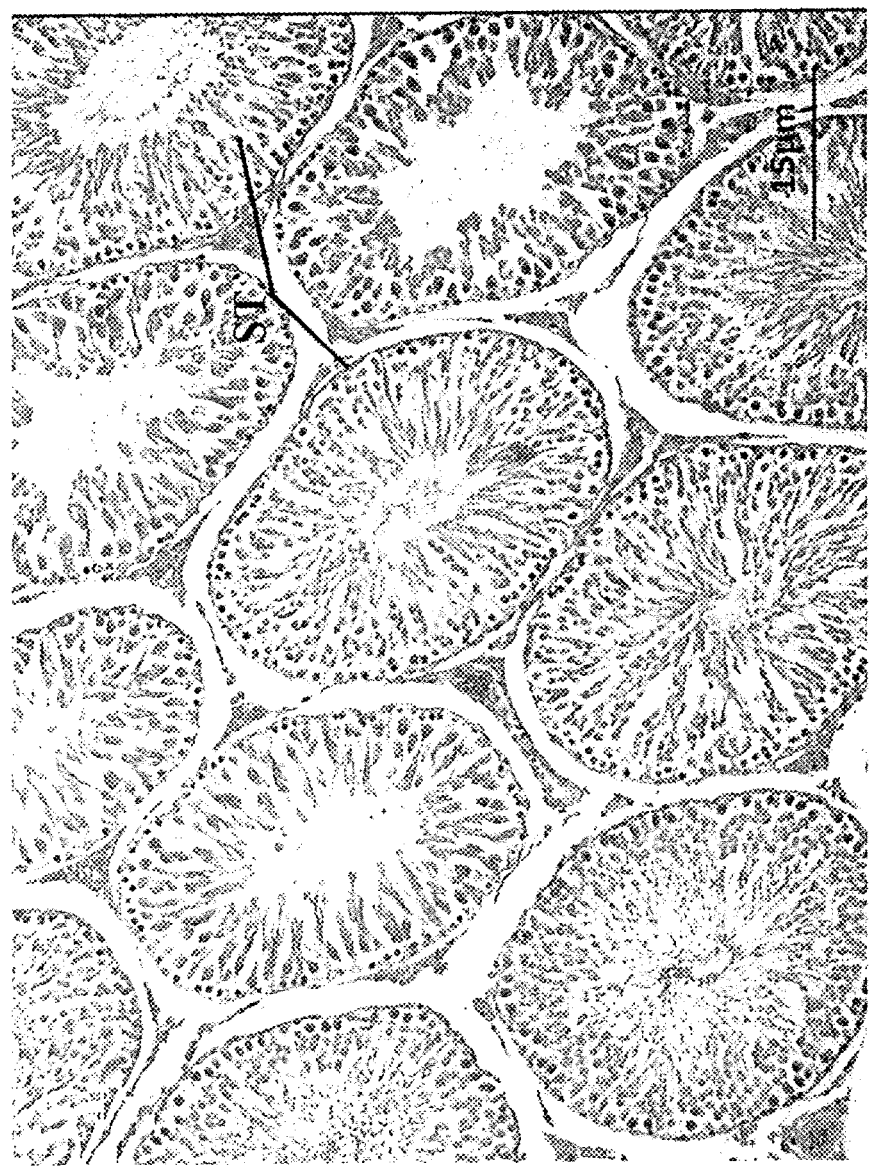
FIG. 4B is a light micrograph of histological examination of the testis of the rats after 90 days of treatment with the root extract of Costus speciosus (GII), showing regular and hyperspermatogenesis within the seminiferous tubules (ST) compared to the spermatogenesis in the rat testis of the control treatment group (GI) shown in FIG. 4A.
Figure 4D:
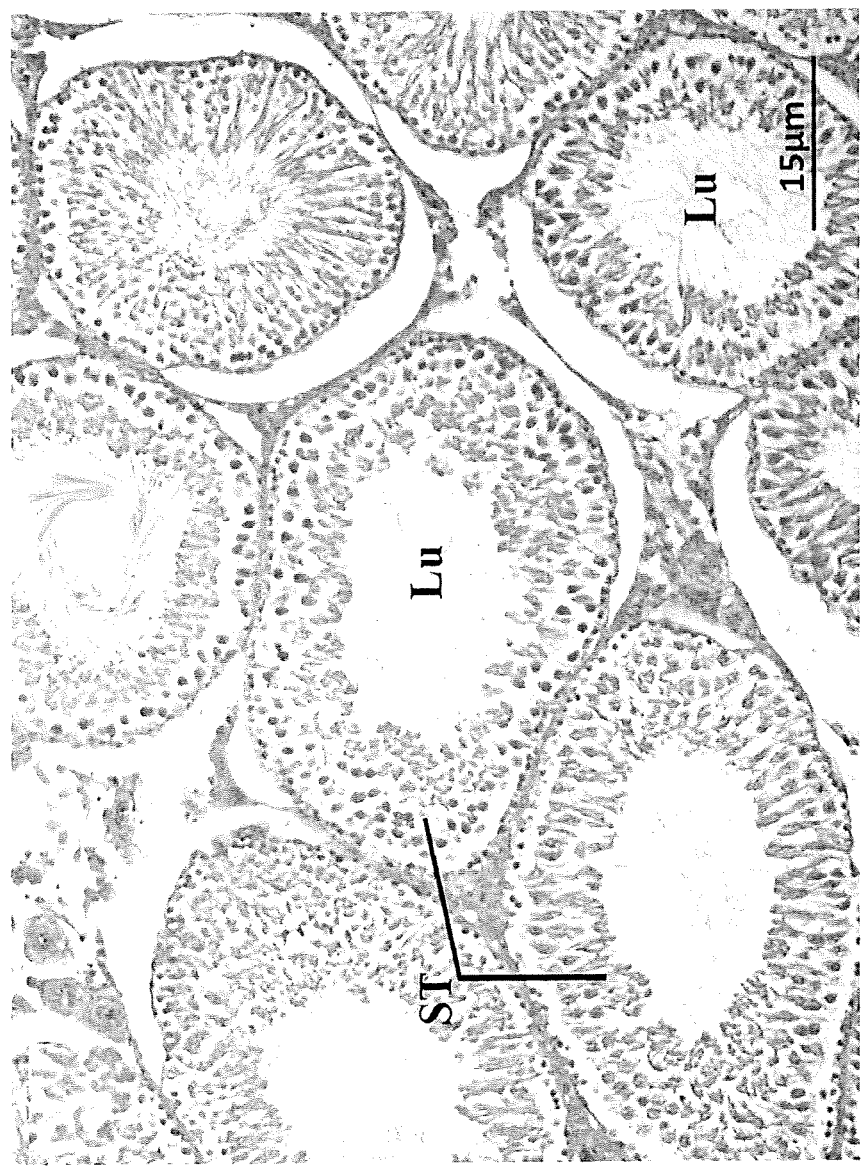
FIG. 4D is a light micrograph of histological examination of the testis of the rats after 90 days of treatment with the root extract of Costus speciosus and the low dose of risperidone (GIV), showing regular different successive stages of spermatogenesis surrounding the central lumens (Lu) of the seminiferous tubules (ST).
Figure 4E:
FIG. 4E is a light micrograph of histological examination of the testis of the rats after 90 days of treatment with the high dose of risperidone (GV), showing degeneration of the germinal epithelium lining (arrowheads), vacuolation of seminiferous tubules (ST) (*), and intertubular oedema (arrows).

3. Histological and Ultrastructural Changes of Testes:

Comparing FIGS. 4C and 4E with FIG. 4A, histological observations of the testes of the rats treated with the low and high doses of risperidone after 90 days revealed the following changes:

(1) Deformation and atrophy of several seminiferous tubules lacking germ cells.

(2) Exfoliation of spermatogenic cells towards the lumina of seminiferous tubules. Spermatogenic cells are cells which regularly replicate and differentiate into mature sperms. Spermatogenic cells are organized in poorly defined layers of progressive development between adjacent Sertoli cells. The most immature spermatogenic cells are spermatogonia that reside on the basal lamina. The most mature spermatogenic cells are spermatids that are attached to the apical portion of the Sertoli cell and border the lumen of the seminiferous tubule.

(3) Separation of spermatogonia from the basement membranes of the seminiferous tubules.

(4) Separation of basal and adluminal cellular compartments in some seminiferous tubules.

(5) Increased space between sperm cells and Sertoli cells.

(6) Necrosis of spermatogenic cells with pyknotic nuclei.

(7) Loss of sperm cells in most lumina of seminiferous tubules.

(8) An increase in intertubular connective tissue (mainly collagen fibers).

(9) Cellular leakage and dilatation of blood vessels with red blood cell stasis.

(10) The severity of the pathologic changes in the testis being proportional to the increase in the cumulative dose of risperidone.

Figure 7A:
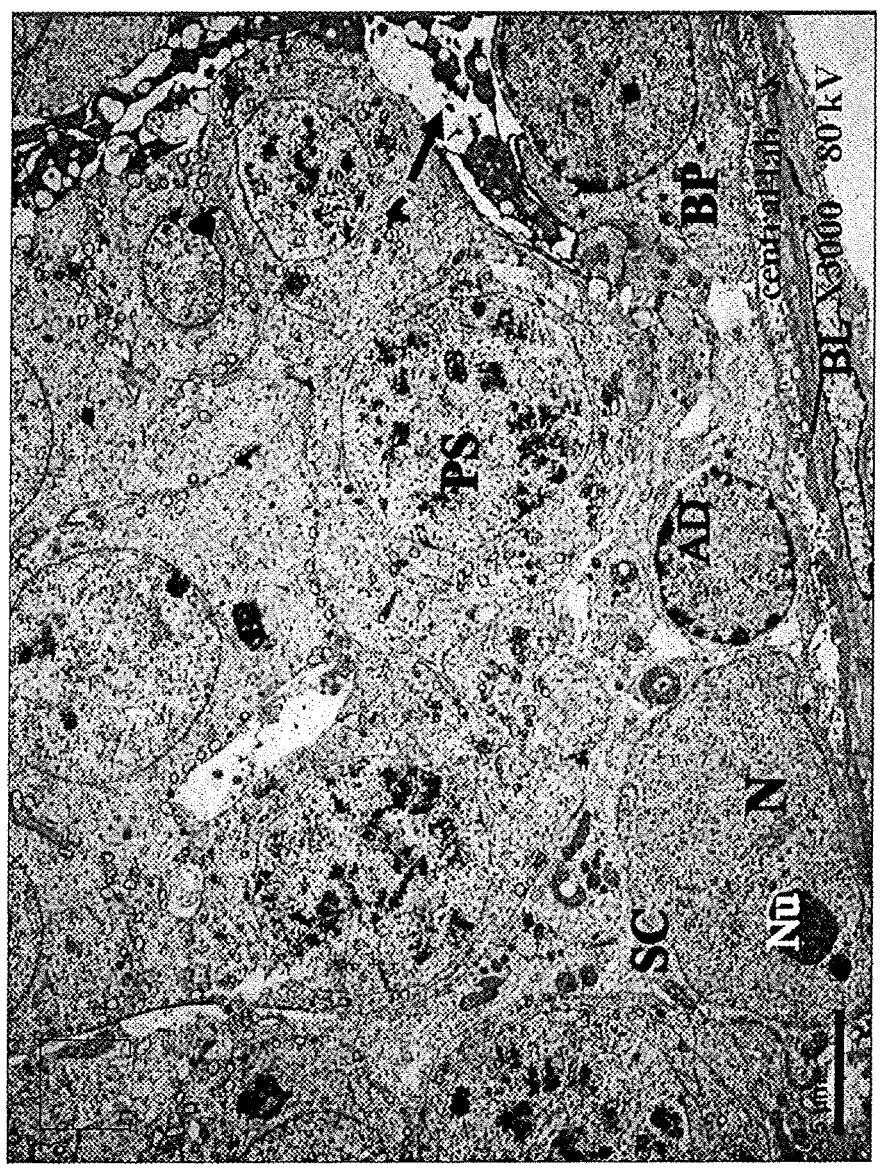
FIG. 7A is a transmission electron micrograph (TEM) of ultrastructural examination of the testis of the rats after 90 days of treatment with the high dose of risperidone (GV), showing dense chromatin of primary spermatocytes (PS), phagolysosome (arrow), type B pale spermatogonia (BP), and the nucleus (N) and nucleolus (Nu) of Sertoli cell (SC).
Figure 7B:
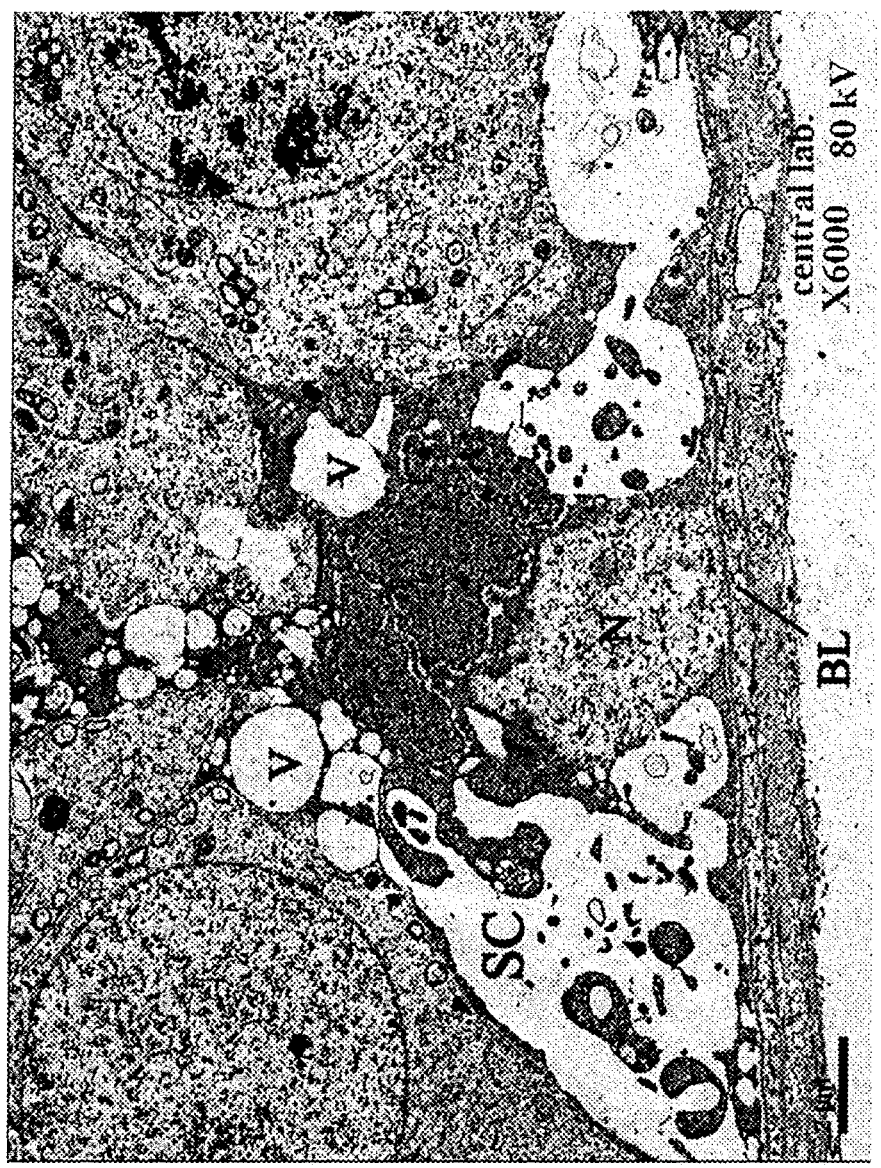
FIG. 7B is a transmission electron micrograph (TEM) of ultrastructural examination of the testis of the rats after 90 days of treatment with the high dose of risperidone (GV), showing karyorrhexis of Sertoli cell (SC) with a highly vacuolated cytoplasm (V).
Figure 7C:
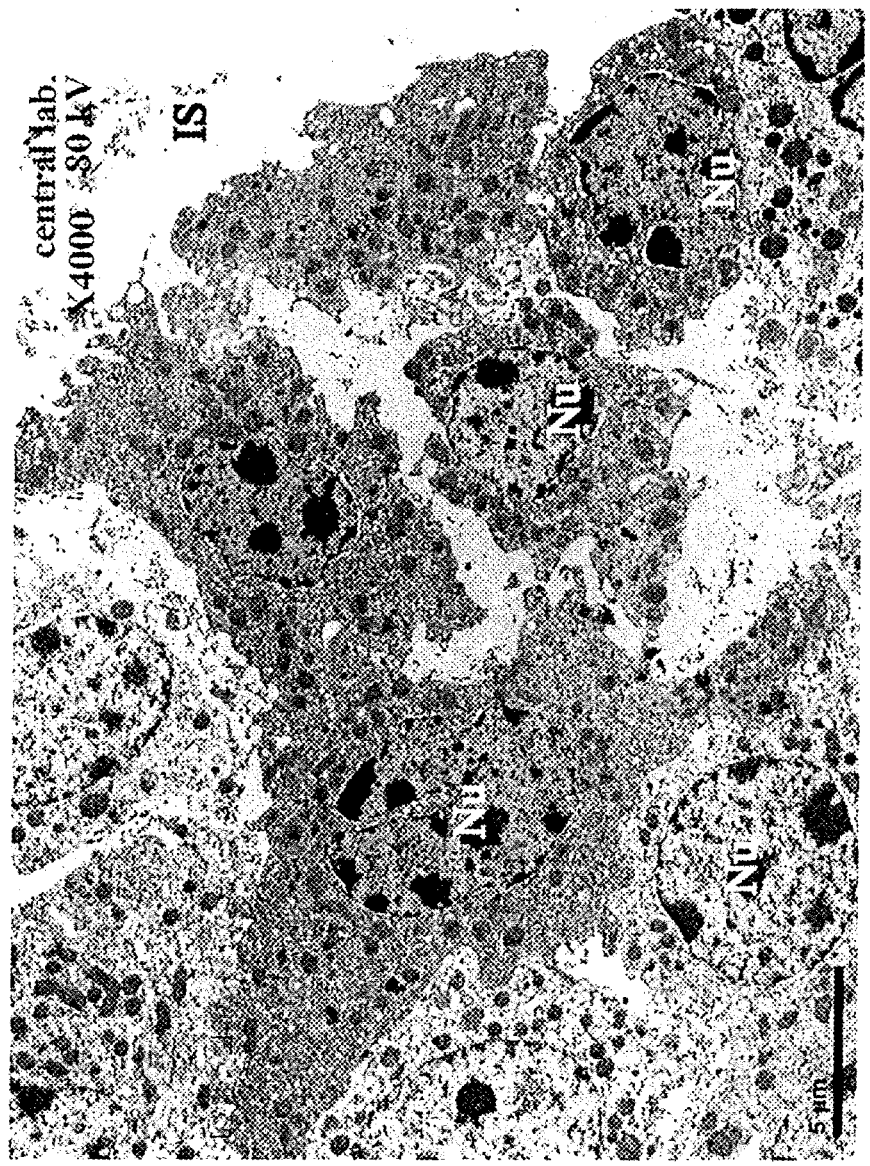
FIG. 7C is a transmission electron micrograph (TEM) of ultrastructural examination of the testis of the rats after 90 days of treatment with the high dose of risperidone (GV), showing interstitial space (IS) and Leydig cells with marginated multinucleoli (Nu).

Referring to FIGS. 7A-7C, the ultrastructural changes of the testis of the rats treated with the high dose of risperidone for 90 days included:

(1) Disorganization of seminiferous tubules due to disappearance of spermatogenic cells.

(2) Pyknotic and dark nuclei with high electron density of spermatogenic cells, e.g. spermatogonia.

(3) Vacuolar degeneration in the cytoplasm of type B (pale) spermatogonia (i.e. differentiating progenitors that form spermatocytes). Type B (pale) spermatogonia are characterized by round or slightly ovoid nuclei containing large clumps of chromatin adjacent to the nuclear envelope and a centrally located nucleolus. The cytoplasm of type B (pale) spermatogonia stains lightly and has a faint granular texture (See Histology: A Text and Atlas, with Correlated Cell and Molecular Biology, 6th Edition 6th Edition, by Michael H. Ross and Wojciech Pawlina, incorporated herein by reference in its entirety).

(4) Aggregation of early spermatids in the lumen of seminiferous tubules. Spermiogenesis refers specifically to the differentiation of early spermatids into mature spermatids just before their release into the seminiferous tubule lumen. Major features of spermiogenesis include elaboration of the acrosome from the Golgi apparatus, condensation and elongation of the nucleus, formation of a motile flagellum, and extensive shedding of the cytoplasm.

(5) Atrophied Sertoli cells with degenerate cytoplasmic organelles, e.g. swollen mitochondria, widening ER, and with a proliferation of vacuoles in the cytoplasm.

(6) Separation of spermatocyte from Sertoli cells.

(7) An increased number of Leydig cells in the intertubular space.

Referring to FIG. 4B and FIGS. 6A-6C, no histological or ultrastructural alterations were observed in the testes of the rats treated with the root extract of Costus speciosus only.

Figure 4F:
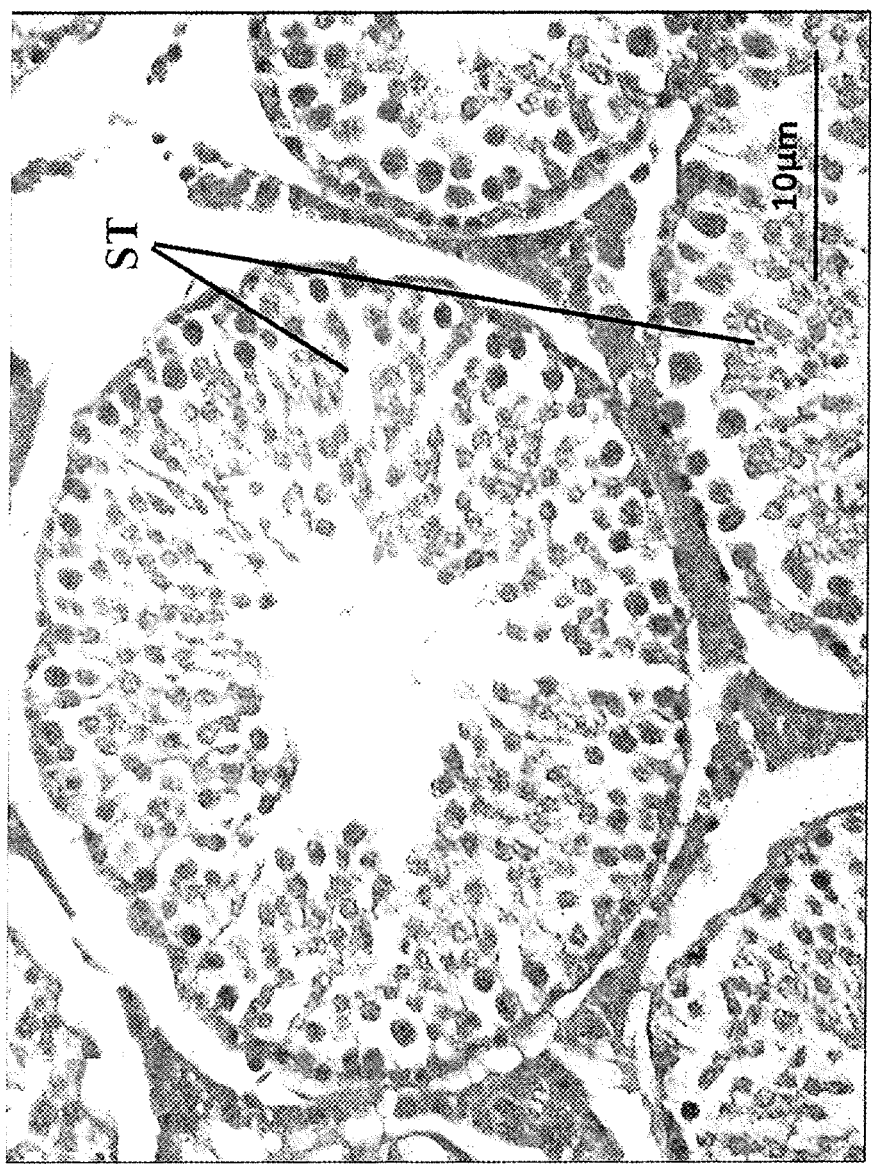
FIG. 4F is a light micrograph of histological examination of the testis of the rats after 90 days of treatment with the root extract of Costus speciosus and the high dose of risperidone (GVI), showing eosinophilic fibrillar interstitium and evident restoration of spermatogenesis within regular circular seminiferous tubules (ST) as compared with FIG. 4E.

Referring to FIGS. 4D and 4F, histological examination of the testes of the rats treated with both the root extract of Costus speciosus and risperidone at the low or high dose after 90 days revealed:

(1) Seminiferous tubules with a regular architecture more or less similar to those in the testes of the rats of the control treatment group.

(2) Spermatogenic cells in regularly arranged rows with different stages of spermatogenesis, especially sperm cells in the lumen.

Figure 5A:
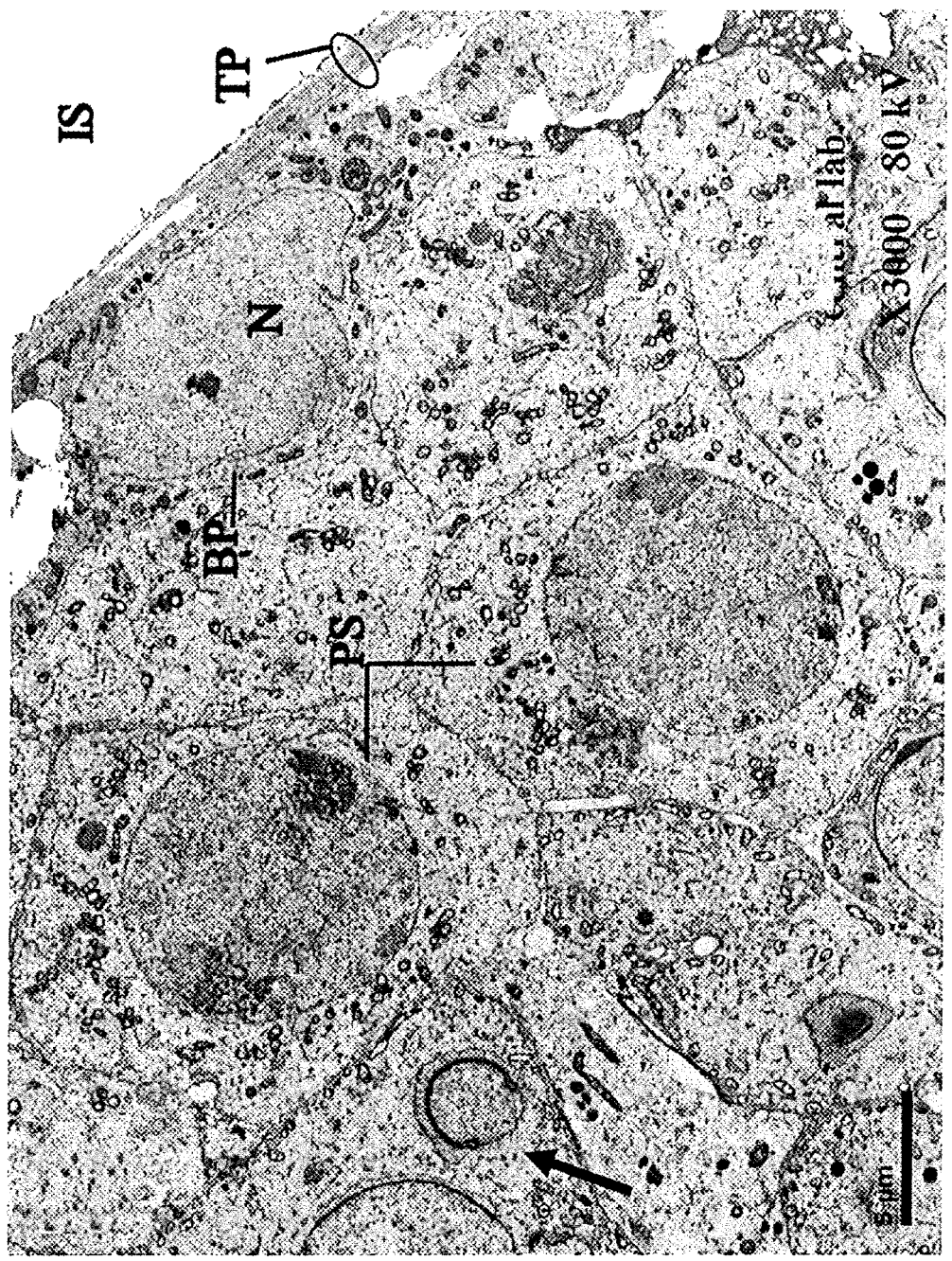
FIG. 5A is a transmission electron micrograph (TEM) of ultrastructural examination of the rat testis of the control treatment group (GI) after 90 days of treatment, showing different types of germinal epithelium: type B pale spermatogonia (BP), nucleus (N) of primary spermatocytes (PS), very early spermatid (arrow), tunica propria (TP), and testicular interstitium (IS).
Figure 5B:
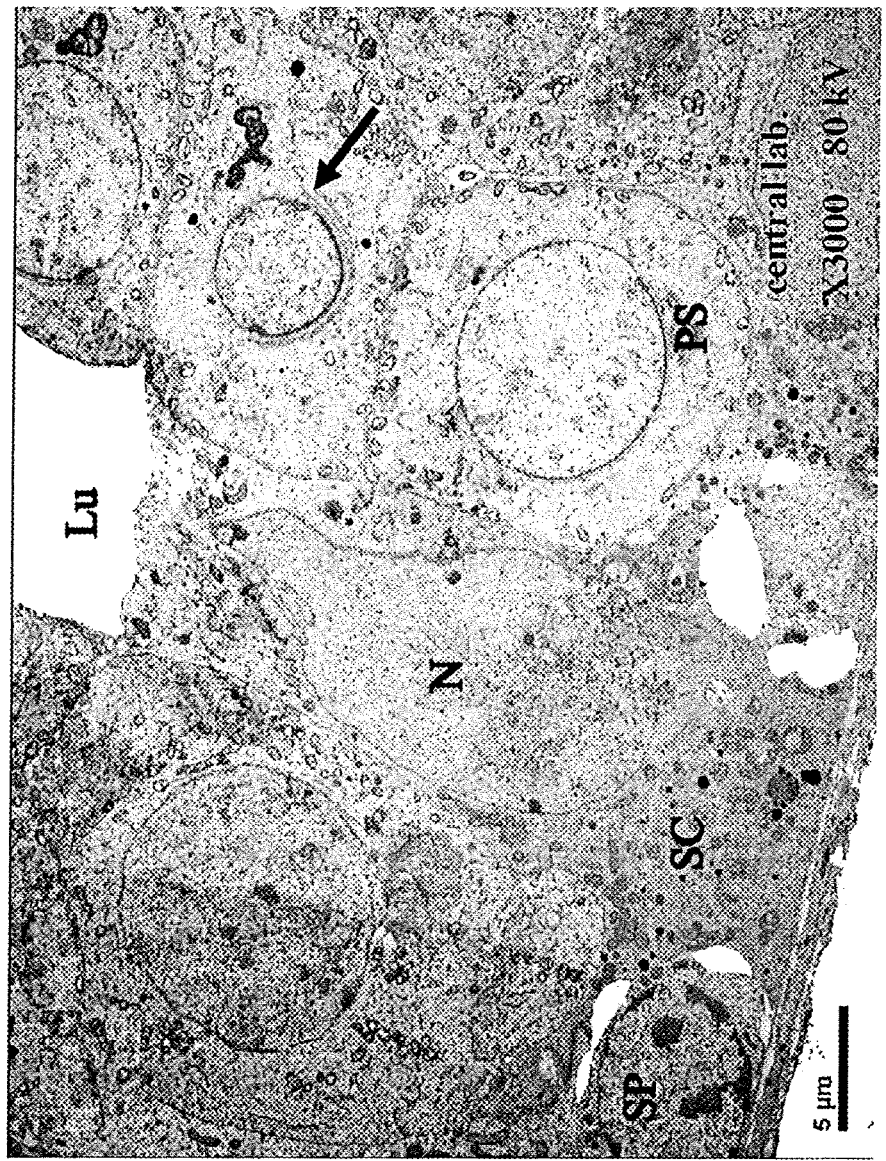
FIG. 5B is a transmission electron micrograph (TEM) of ultrastructural examination of the rat testis of the control treatment group (GI) after 90 days of treatment, showing spermatogonia (SP), primary spermatocyte (PS), very early spermatid formation (arrow), and a Sertoli cell (SC) extending from the basal lamina to the luminal surface (Lu) of the seminiferous epithelium with a large nucleus (N) which is lightly stained and of which long axis is oriented perpendicular to the wall of the tubule.
Figure 5C:
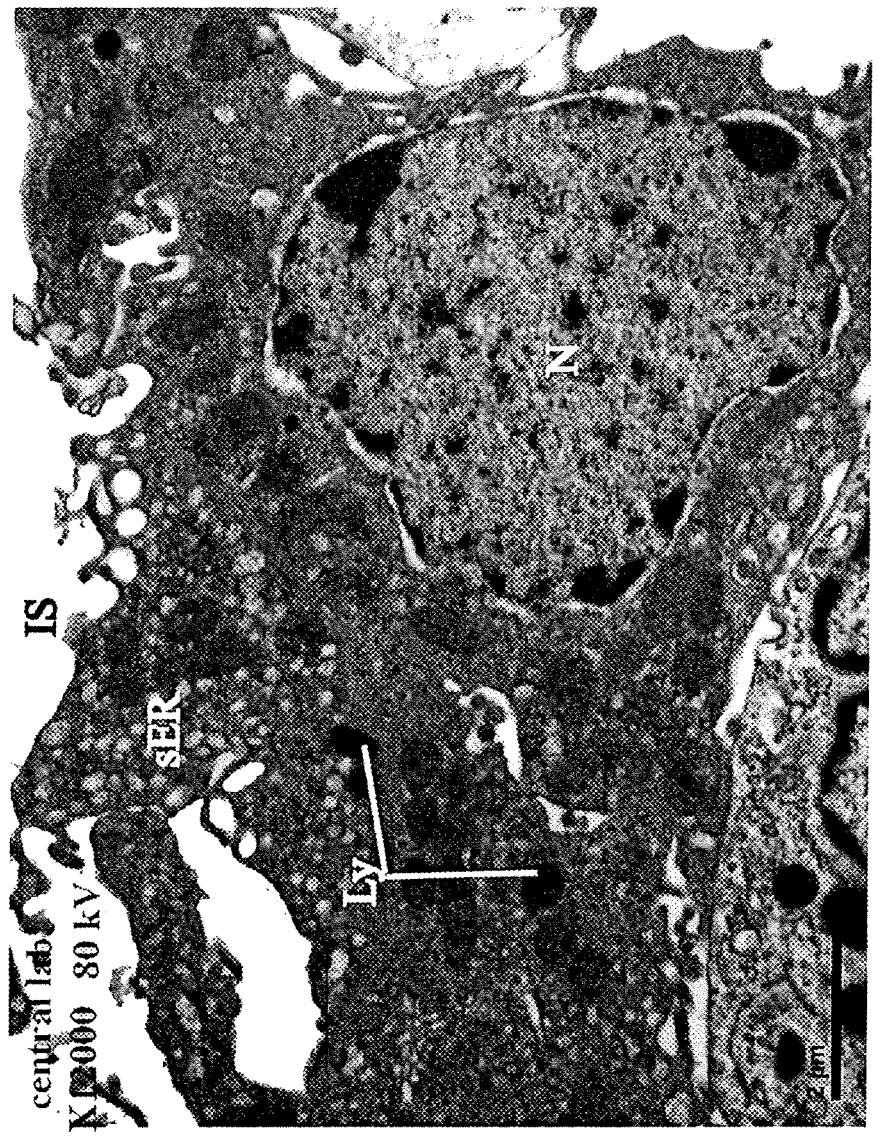
FIG. 5C is a transmission electron micrograph (TEM) of ultrastructural examination of the rat testis of the control treatment group (GI) after 90 days of treatment, showing interstitial space (IS) and a portion of a Leydig cell, including the cytoplasm containing an abundance of smooth endoplasmic reticulum (sER), the nucleus (N), and lysosomes (Ly).
Figure 6A:
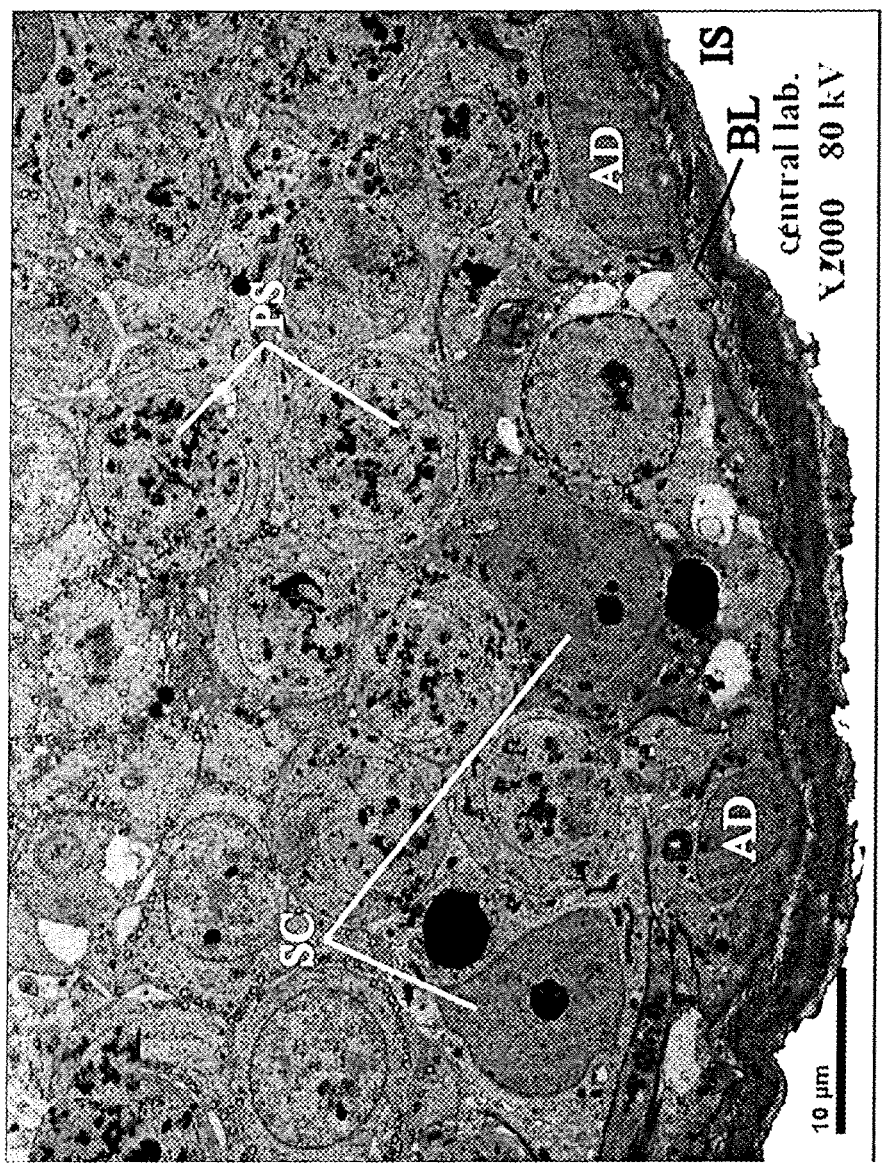
FIG. 6A is a transmission electron micrograph (TEM) of ultrastructural examination of the testis of the rats after 90 days of treatment with the root extract of Costus speciosus (GII), showing normal testicular architecture with regular course of spermatogenesis as compared to the testis of the rats of the control treatment group (GI), type A dark (AD) spermatogonia (SG), active primary spermatocytes (PS), intertubular space (IS), basal lamina (BL), and proliferation of Sertoli cells (SC).
Figure 6B:
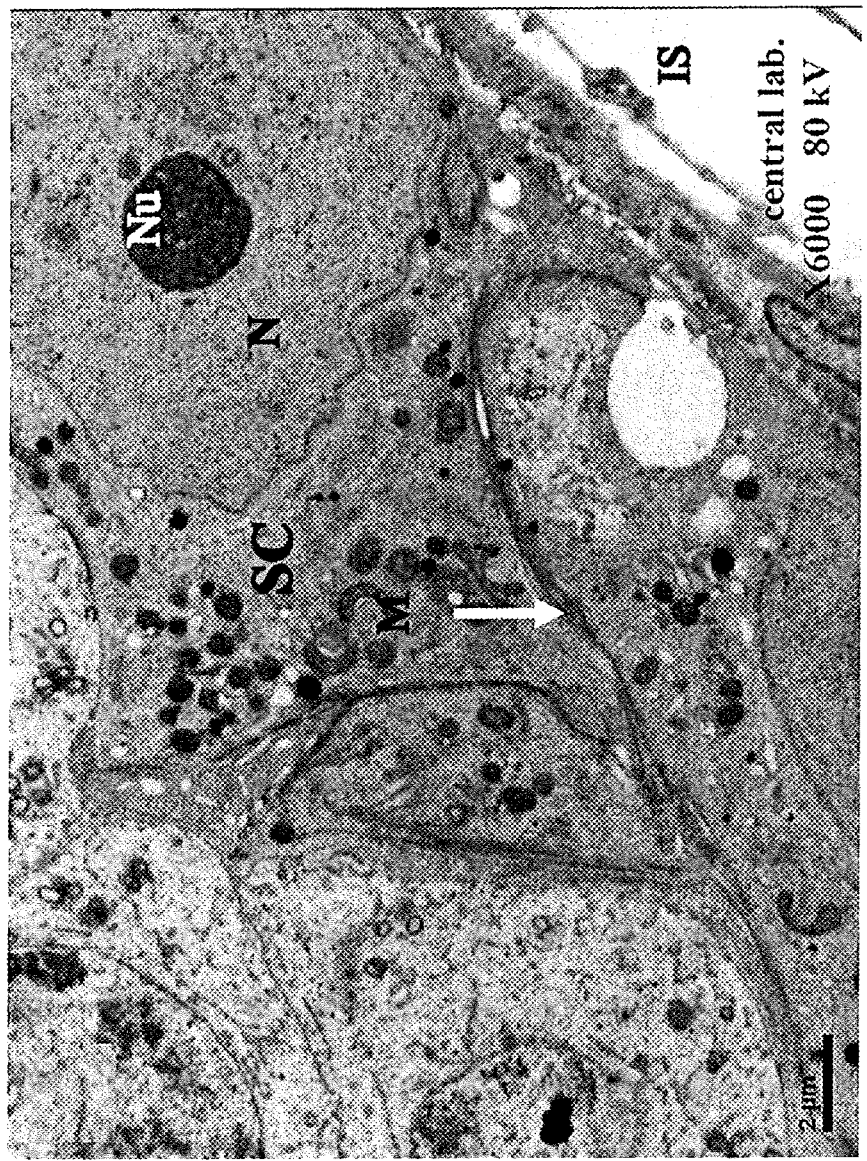
FIG. 6B is a transmission electron micrograph (TEM) of ultrastructural examination of the testis of the rats after 90 days of treatment with the root extract of Costus speciosus (GII), showing a blood testis barrier and a part of a seminiferous tubule including a Sertoli cell (SC) with the nucleus (N), a prominent nucleolus (Nu) indicating high activity, and numerous distinct mitochondria (M).
Figure 6C:
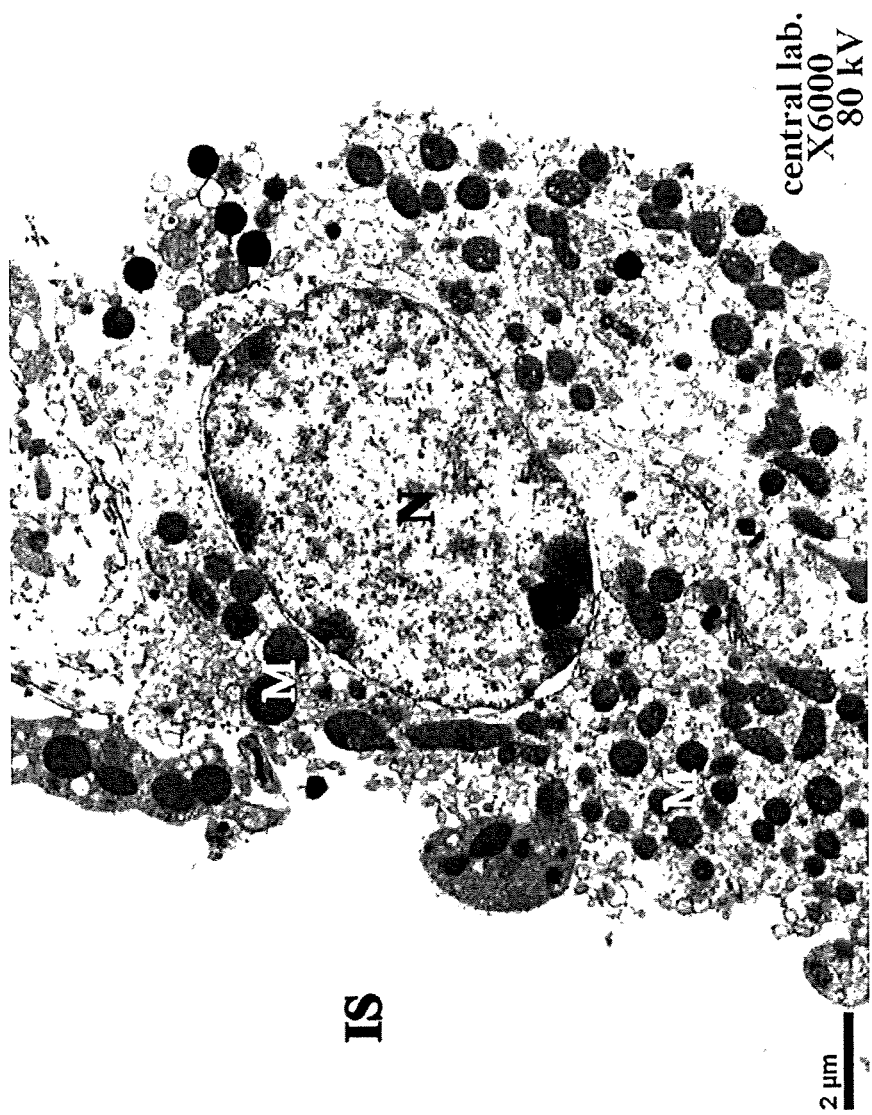
FIG. 6C is a transmission electron micrograph (TEM) of ultrastructural examination of the testis of the rats after 90 days of treatment with the root extract of Costus speciosus (GII), showing a Leydig cell with a large number of mitochondria (M) as compared with the Leydig cell in the rat testis of the control treatment group (GI).

(3) Intertubular tissue more or less similar to that in the testes of the rats of the control treatment group shown in FIGS. 5A-5C.

Figure 8A:
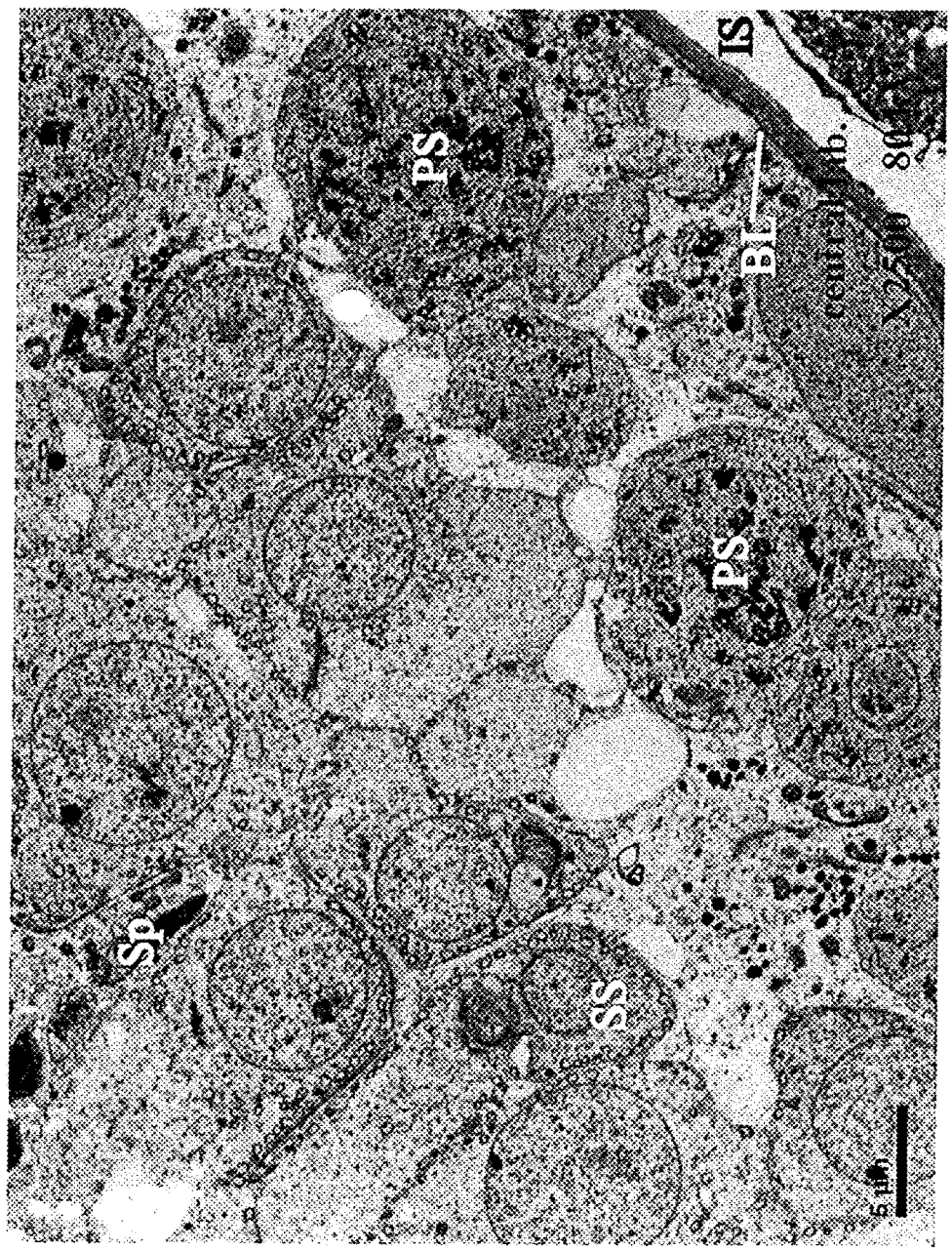
FIG. 8A is a transmission electron micrograph (TEM) of ultrastructural examination of the testis of the rats after 90 days of treatment with the root extract of Costus speciosus and the high dose of risperidone (GVI), showing normal testicular architecture with the regular course of spermatogenesis, primary spermatocyte (PS), secondary spermatocyte (SS), basal lamina (BL), and interstitial space (IS).
Figure 8B:
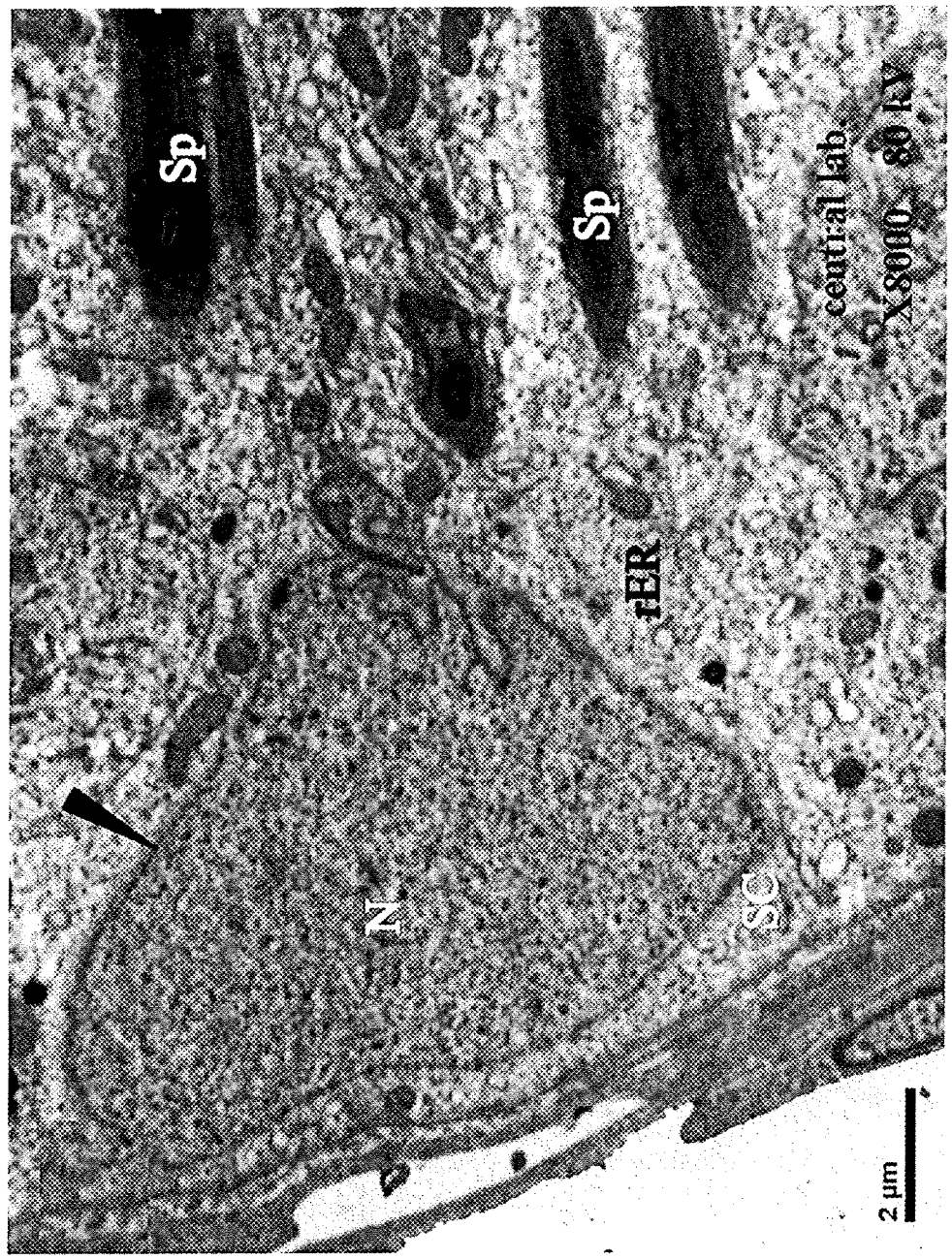
FIG. 8B is a transmission electron micrograph (TEM) of ultrastructural examination of the testis of the rats after 90 days of treatment with the root extract of Costus speciosus and the high dose of risperidone (GVI), showing Sertoli cell (SC) with regular nuclear envelope (arrowhead), as well as developing spermatozoa embedded in the Sertoli cell cytoplasm.
Figure 8C:
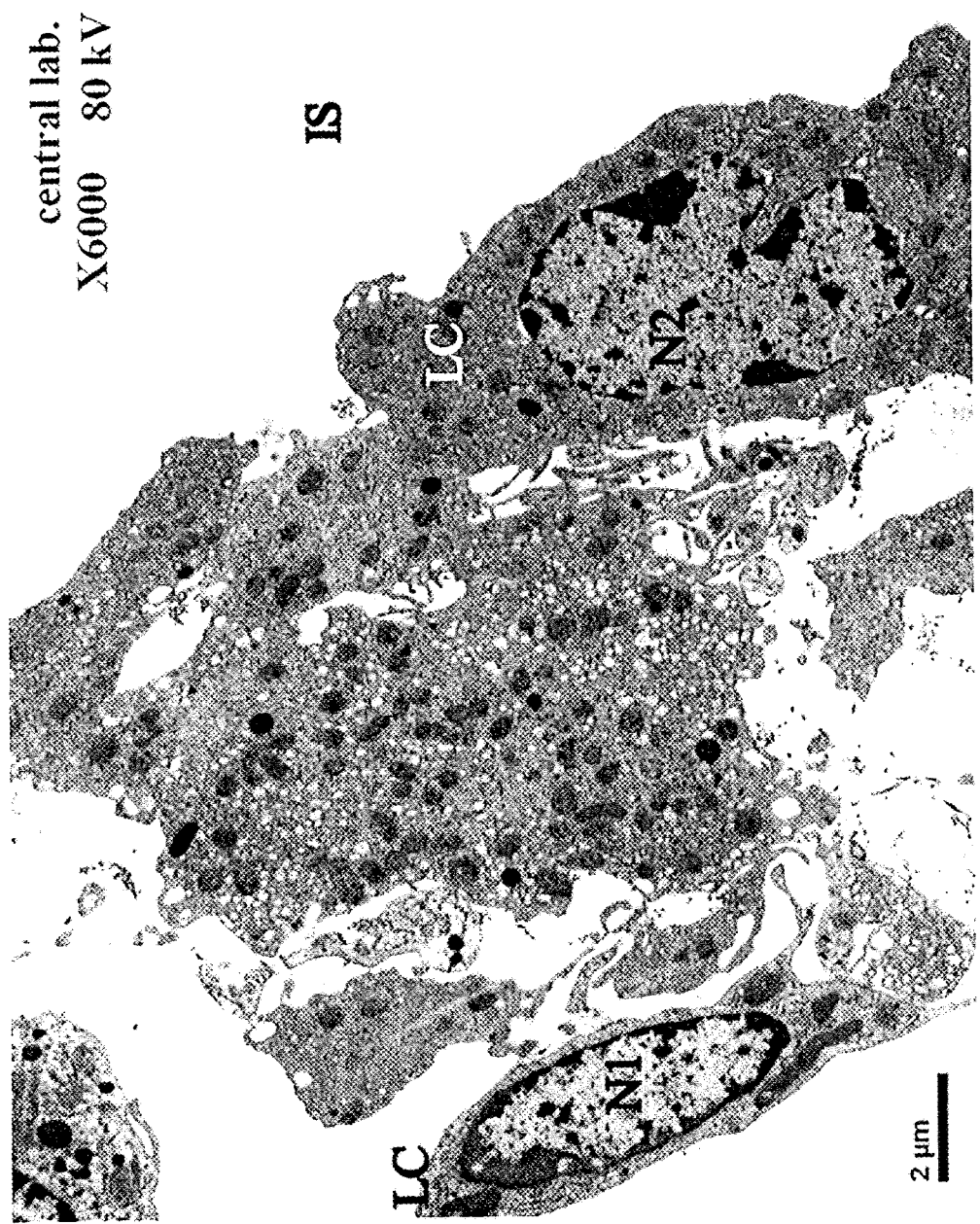
FIG. 8C is a transmission electron micrograph (TEM) of ultrastructural examination of the testis of the rats after 90 days of treatment with the root extract of Costus speciosus and the high dose of risperidone (GVI), showing Leydig cell (LC) with a regular nuclear envelope of nuclei (N1, N2), almost disappearance of folded invaginated cleft and multiple nucleoli, and interstitial space (IS).
Figure 9:
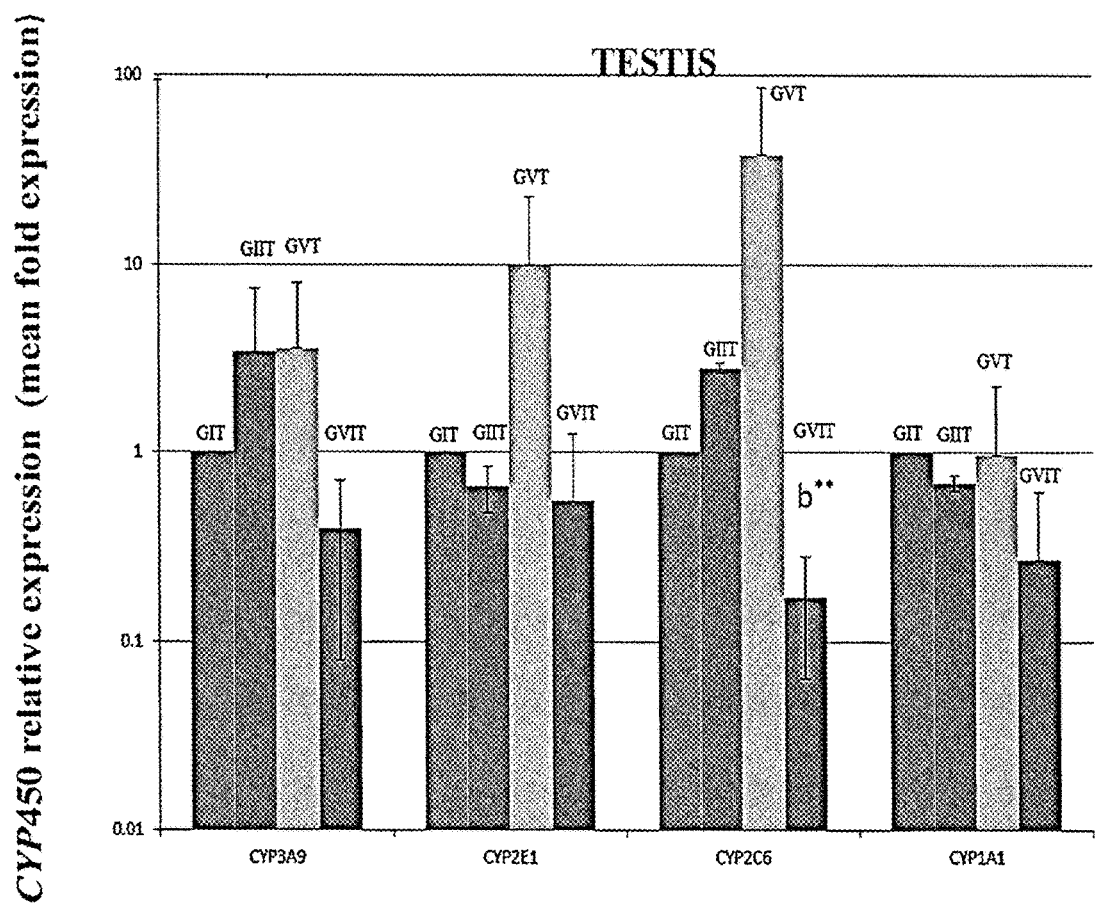
FIG. 9 is a graphical presentation of the quantitative real-time PCR results showing the means±standard deviations of the mRNA expression levels of the indicated cytochrome P450 genes in the testis of the rats of the first treatment group (GIT) taken as 1, the second treatment group (GIIT), the fifth treatment group (GVT), and the sixth treatment group (GVIT) after 90 days of treatment, with 5 rats in each treatment group. b denotes a pairwise comparison of the mRNA expression levels of the same cytochrome P450 gene between the instant treatment group and GIIT. ** $P<0.01$.
Figure 10A:
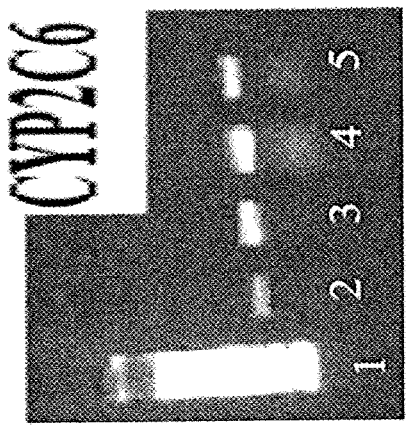
FIG. 10A is an image of an ethidium bromide stained agarose gel showing the results of semi-quantitative PCR comparing relative levels of CYP3A9 mRNA expression in the rat testes of various treatment groups: GIT (lane 2); GIIT (lane 3); GVT (lane 4), and GVIT (lane 5). Lane 1 is a DNA molecular weight marker.
Figure 10B:
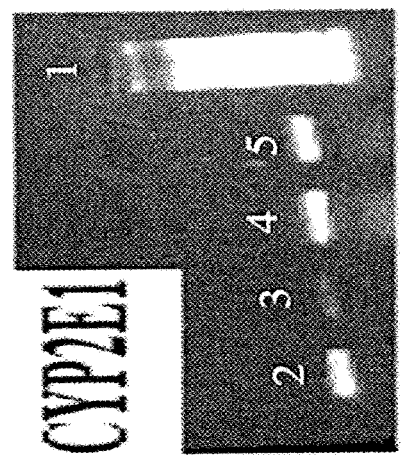
FIG. 10B is an image of an ethidium bromide stained agarose gel showing the results of semi-quantitative PCR comparing relative levels of CYP2E1 mRNA expression in the rat testes of various treatment groups: GIT (lane 2); GIIT (lane 3); GVT (lane 4), and GVIT (lane 5). Lane 1 is a DNA molecular weight marker.
Figure 10C:
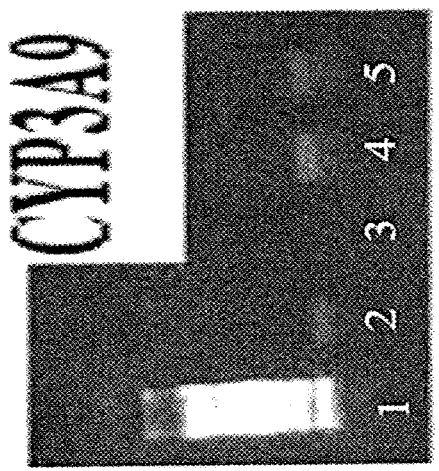
FIG. 10C is an image of an ethidium bromide stained agarose gel showing the results of semi-quantitative PCR comparing relative levels of CYP2C6 mRNA expression in the rat testes of various treatment groups: GIT (lane 2); GIIT (lane 3); GVT (lane 4), and GVIT (lane 5). Lane 1 is a DNA molecular weight marker.
Figure 10E:
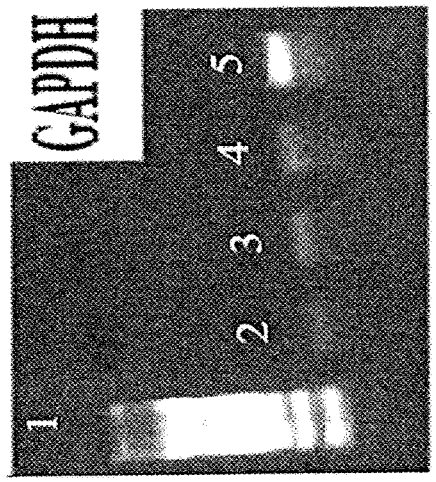
FIG. 10E is an image of an ethidium bromide stained agarose gel showing the results of semi-quantitative PCR for the reference gene GAPDH mRNA expression levels in the rat testes of various treatment groups for normalizing the mRNA expression levels of CYP3A9, CYP2E1, CYP2C6, and CYP1A1: GIT (lane 2); GIIT (lane 3); GVT (lane 4), and GVIT (lane 5). Lane 1 is a DNA molecular weight marker.
Figure 10D:
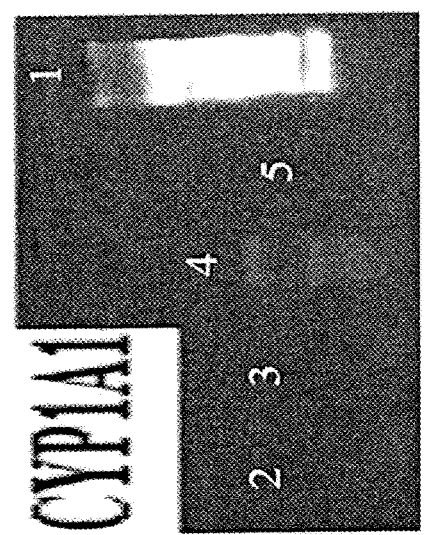
FIG. 10D is an image of an ethidium bromide stained agarose gel showing the results of semi-quantitative PCR comparing relative levels of CYP1A1 mRNA expression in the rat testes of various treatment groups: GIT (lane 2); GIIT (lane 3); GVT (lane 4), and GVIT (lane 5). Lane 1 is a DNA molecular weight marker.

Referring to FIGS. 8A-8C, the ultrastructural examination of the testes of the rats treated with the high dose of risperidone as well as the root extract of Costus speciosus for 90 days revealed:

(1) Recognizable developmental stages of spermatogenic epithelium including spermatid (Sp), secondary spermatocyte (SS), and primary spermatocyte (PS).

(2) Sertoli cells as elongated cells with giant nuclei, prominent nucleoli, ER and mitochondria.

(3) The intertubular space has a moderate number of Leydig cells and regular blood vessels.

In general, co-treatment with risperidone and the root extract of Costus speciosus inhibited the histopathological alterations induced by risperidone within the testes.

4. Molecular Changes:

Referring to FIG. 9 and FIGS. 10A-10E for the quantitative real-time PCR results and the semi-quantitative PCR results, respectively, the oral administration of the high dose of risperidone to the rats for 90 days (GVT) induced some changes in the mRNA expression levels of some cytochrome P450 genes in the testes of the rats, specifically, an increase in the mRNA expression levels of CYP3A9, CYP2E1, and CYP2C6 genes and a decrease in the mRNA expression level of CYP1A1 gene as compared to the corresponding mRNA expression levels in the control treatment group (GIT).

The oral administration of the root extract of Costus speciosus to the rats for 90 days (GIIT) induced a decrease in the mRNA expression levels of CYP2E1 and CYP1A1 genes and an increase in the mRNA expression levels of CYP2C6 and CYP3A9 genes in the testes of the rats, as compared to the corresponding mRNA expression levels in the control treatment group (GIT).

The oral administration of the root extract of Costus speciosus in combination with the high dose of risperidone to the rats for 90 days (GVIT) induced a decrease in the mRNA expression levels of all of the cytochrome P450 genes tested, i.e. CYP3A9, CYP2E1, CYP2C6, and CYP1A1 genes in the testes of the rats, as compared to the corresponding mRNA expression levels in the control treatment group (GIT). Further, the mRNA expression level of CYP2C6 decreased significantly in the testes of the rats treated with the root extract of Costus speciosus in combination with the high dose of risperidone (GVIT) as compared to that in the testes of the rats treated with the root extract of Costus speciosus only (GIIT), indicating that the co-treatment of the root extract of Costus speciosus reduced risperidone-induced cellular toxicity.

The invention claimed is:

1. A method of increasing fertility of a male subject suffering from reduced fertility resulting from a medication from at least one antipsychotic drug, the method comprising:
administering to the male subject an effective amount of an extract of Costus speciosus in combination with the medication,
wherein the medication inhibits sperm cell production by inhibiting spermatogenesis in a testis of the male subject and the administering the extract of Costus speciosus reduces the inhibition of sperm cell production by the medication, resulting in increasing fertility of the male subject.

2. The method of claim 1, wherein the male subject is a male human or a non-human male mammal.

3. The method of claim 1, wherein the medication inhibiting the spermatogenesis in the testis of the male subject results in at least one selected from the group consisting of (a) deformation and/or atrophy of one or more seminiferous tubules lacking germ cells, (b) exfoliation of spermatogenic cells towards a lumen of a seminiferous tubule, (c) separation of spermatogonia from a basement membrane of a seminiferous tubule, (d) separation of a basal and/or an adluminal cellular compartment in a seminiferous tubule, (e) an increased space between sperm cells and Sertoli cells, (f) necrosis of spermatogenic cells, (g) loss of sperm cells in 70-100% of lumina of seminiferous tubules, (h) aggregation of spermatids in one or more lumina of seminiferous tubules, (i) atrophy of Sertoli cells, and (j) separation of spermatocytes from Sertoli cells.

4. The method of claim 1, wherein the medication inhibiting sperm cell production results in a 10-100% reduction in a sperm count of the male subject relative to a baseline sperm count of the male subject before the medication is administered to the male subject.

5. The method of claim 1, wherein the medication comprises at least one antipsychotic drug selected from the group consisting of a typical antipsychotic drug and an atypical antipsychotic drug.

6. The method of claim 5, wherein the male subject suffers from schizophrenia, and the at least one antipsychotic drug is for treating schizophrenia.

7. The method of claim 6, wherein the at least one antipsychotic drug for treating schizophrenia is selected from the group consisting of olanzapine, risperidone, and clozapine.

8. The method of claim 1, wherein the extract of Costus speciosus is at least one selected from the group consisting of an extract of Costus speciosus leaves, an extract of Costus speciosus roots, an extract of Costus speciosus flowers, an extract of Costus speciosus rhizomes, and an extract of Costus speciosus stems.

9. The method of claim 1, wherein the extract of Costus speciosus is in a form selected from the group consisting of a solid, a semi-solid, and a liquid.

10. The method of claim 1, wherein the extract of Costus speciosus comprises at least one selected from the group consisting of tocopherols, phenols, flavanoids, alkaloids, terpenoids, steroids, tannins, phenolic acids, glycosides, carbohydrates, aliphatic hydroxyl ketones, triterpenes, oxoacids, fatty acids, and minerals.

11. The method of claim 1, wherein the extract of Costus speciosus comprises at least one flavonoid selected from the group consisting of quercetin, rutin, and apigenin.

12. The method of claim 1, wherein the extract of Costus speciosus is administered orally, by inhalation, and/or transdermally.

13. The method of claim 1, wherein the extract of Costus speciosus is administered daily, twice a week, weekly, once every two weeks, once every three weeks, monthly, or at a variable interval.

14. The method of claim 1, wherein the extract of Costus speciosus is administered as the sole agent to reduce the inhibition of sperm cell production by the medication and/or to increase the fertility of the male subject.

15. The method of claim 1, wherein the male subject is a male human and the extract of Costus speciosus is administered in the effective amount of 1-100 mg dry extract/kg body weight/day.

16. The method of claim 1, wherein the administration of the extract of Costus speciosus in combination with the medication results in a 10-1000% increase in a sperm count of the male subject as compared to a sperm count of a control male subject administered with the medication but not the extract of Costus speciosus.

17. The method of claim 1, wherein the administration of the extract of Costus speciosus in combination with the medication increases a sperm count of the male subject to within a normal range.

* * * * *

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: Synthetic forward primer

<400> SEQUENCE: 1
gggaggttac tggttctgg                                                19

<210> SEQ ID NO 2
<211> LENGTH: 20
<212> TYPE: DNA
<213> ORGANISM: Artificial Sequence
<220> FEATURE:
<223> OTHER INFORMATION: Synthetic reverse primer

<400> SEQUENCE: 2
atgaggctgt ctgtgatgtc                                               20

<210> SEQ ID NO 3
<211> LENGTH: 20
<212> TYPE: DNA
<213> ORGANISM: Artificial Sequence
```

```
<220> FEATURE:
<223> OTHER INFORMATION: Synthetic forward primer

<400> SEQUENCE: 3
gacctcattc ctaccaacct                                             20

<210> SEQ ID NO 4
<211> LENGTH: 18
<212> TYPE: DNA
<213> ORGANISM: Artificial Sequence
<220> FEATURE:
<223> OTHER INFORMATION: Synthetic reverse primer

<400> SEQUENCE: 4
cctctcctgc acacatcc                                               18

<210> SEQ ID NO 5
<211> LENGTH: 19
<212> TYPE: DNA
<213> ORGANISM: Artificial Sequence
<220> FEATURE:
<223> OTHER INFORMATION: Synthetic forward primer

<400> SEQUENCE: 5
cctttccctc ttcccatcc                                              19

<210> SEQ ID NO 6
<211> LENGTH: 19
<212> TYPE: DNA
<213> ORGANISM: Artificial Sequence
<220> FEATURE:
<223> OTHER INFORMATION: Synthetic reverse primer

<400> SEQUENCE: 6
aacctccgca catccttcc                                              19

<210> SEQ ID NO 7
<211> LENGTH: 23
<212> TYPE: DNA
<213> ORGANISM: Artificial Sequence
<220> FEATURE:
<223> OTHER INFORMATION: Synthetic forward primer

<400> SEQUENCE: 7
ggtgttgtat cacatggacc aga                                         23

<210> SEQ ID NO 8
<211> LENGTH: 24
<212> TYPE: DNA
<213> ORGANISM: Artificial Sequence
<220> FEATURE:
<223> OTHER INFORMATION: Synthetic reverse primer

<400> SEQUENCE: 8
ccaggagtga acaaaattac tgca                                        24

<210> SEQ ID NO 9
<211> LENGTH: 19
<212> TYPE: DNA
<213> ORGANISM: Artificial Sequence
<220> FEATURE:
<223> OTHER INFORMATION: Synthetic forward primer

<400> SEQUENCE: 9
gatggtgaag gtcggtgtg                                              19
```

```
<210> SEQ ID NO 10
<211> LENGTH: 19
<212> TYPE: DNA
<213> ORGANISM: Artificial Sequence
<220> FEATURE:
<223> OTHER INFORMATION: Synthetic reverse primer

<400> SEQUENCE: 10
atgaatgggt cgttgatgg                                              19
```